(12) United States Patent  (10) Patent No.: US 8,579,859 B2
Kramer et al.  (45) Date of Patent: Nov. 12, 2013

(54) FLUID BALANCE MONITORING SYSTEM WITH FLUID INFUSION PUMP FOR MEDICAL TREATMENT

(75) Inventors: George C. Kramer, Galveston, TX (US); Guy A. Drew, San Antonio, TX (US); Donald J. Deyo, Galveston, TX (US); Allen E. Brandenburg, Dripping Springs, TX (US); Richard B. Voigt, Texas City, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 102 days.

(21) Appl. No.: 12/978,692

(22) Filed: Dec. 27, 2010

(65) Prior Publication Data

US 2011/0196304 A1 Aug. 11, 2011

Related U.S. Application Data

(60) Provisional application No. 61/290,188, filed on Dec. 26, 2009.

(51) Int. Cl.
*A61M 1/00* (2006.01)
(52) U.S. Cl.
USPC .......................................... 604/151; 604/157
(58) Field of Classification Search
USPC ............. 604/65–67, 118, 131, 141, 142, 151, 604/157, 81, 153, 257, 181, 262
See application file for complete search history.

(56) References Cited

U.S. PATENT DOCUMENTS

| | | |
|---|---|---|
| 4,043,332 A | 8/1977 | Metcalf |
| 4,237,881 A | 12/1980 | Beigler |
| 4,291,692 A | 9/1981 | Bowman |
| 4,303,376 A | 12/1981 | Siekmann |
| 4,430,078 A | 2/1984 | Sprague |
| 4,539,005 A | 9/1985 | Greenblatt |
| 4,551,136 A | 11/1985 | Mandl |
| 4,613,327 A | 9/1986 | Tegrarian et al. |
| 4,657,160 A | 4/1987 | Woods et al. |
| 4,666,430 A | 5/1987 | Brown et al. |
| 4,684,367 A | 8/1987 | Schaffer et al. |
| 4,735,613 A | 4/1988 | Bellin et al. |
| 4,857,055 A | 8/1989 | Wang |
| 5,053,011 A | 10/1991 | Strobel et al. |
| 5,059,182 A | 10/1991 | Laing |
| 5,308,335 A | 5/1994 | Ross |
| 5,399,166 A | 3/1995 | Laing |
| 5,492,534 A | 2/1996 | Athayde et al. |

(Continued)

OTHER PUBLICATIONS

Bowman, RJ et al "A microcomputer-based fluid monitoring system for the resuscitation of burn patients" Trans Biomedical Engineering (1981) 28(6):475-479.

(Continued)

*Primary Examiner* — Nicholas Lucchesi
*Assistant Examiner* — Pritesh Patel
(74) *Attorney, Agent, or Firm* — Wong Cabello Lutsch Rutherford & Brucculeri, LLP

(57) ABSTRACT

Novel fluid delivery systems are disclosed to improve the delivery of bio-compatible fluids to a patient. The systems can include a housing having a bladder pressurized by a pressurization unit so that fluid flow rate can be controlled, changed and/or monitored. The systems can also include a scale and/or a flow control unit.

25 Claims, 29 Drawing Sheets

(56) References Cited

U.S. PATENT DOCUMENTS

| | | | |
|---|---|---|---|
| 5,497,912 A | 3/1996 | Hoback et al. | |
| 5,551,849 A | 9/1996 | Christiansen | |
| 5,553,741 A | 9/1996 | Sancoff et al. | |
| 5,554,123 A | 9/1996 | Herskowitz | |
| 5,578,005 A | 11/1996 | Sancoff et al. | |
| RE35,501 E | 5/1997 | Ross et al. | |
| 5,656,033 A | 8/1997 | Atkinson | |
| 5,665,070 A | 9/1997 | McPhee | |
| 5,681,284 A | 10/1997 | Herskowitz | |
| 5,700,245 A | 12/1997 | Sancoff et al. | |
| 5,720,728 A * | 2/1998 | Ford | 604/131 |
| 5,749,854 A | 5/1998 | Shen | |
| 5,938,636 A | 8/1999 | Kramer et al. | |
| 5,954,696 A | 9/1999 | Ryan | |
| 6,056,724 A | 5/2000 | Lacroix | |
| 6,062,429 A | 5/2000 | West et al. | |
| 6,280,416 B1 | 8/2001 | Van Antwerp et al. | |
| 6,398,760 B1 | 6/2002 | Danby | |
| 6,450,991 B1 | 9/2002 | Bunt et al. | |
| 6,458,102 B1 | 10/2002 | Mann et al. | |
| 6,558,346 B1 | 5/2003 | Yoshioka et al. | |
| 6,575,935 B1 | 6/2003 | Oliver et al. | |
| 6,575,961 B2 | 6/2003 | Joshi | |
| 6,595,956 B1 | 7/2003 | Gross et al. | |
| 6,641,562 B1 | 11/2003 | Peterson | |
| 6,767,337 B1 | 7/2004 | Ewerlof | |
| 6,800,069 B2 | 10/2004 | Lampropoulos et al. | |
| 6,802,823 B2 | 10/2004 | Mason | |
| 6,890,320 B2 | 5/2005 | Minezaki | |
| 6,981,960 B2 | 1/2006 | Cho et al. | |
| 7,022,107 B1 | 4/2006 | Christensen et al. | |
| 7,351,226 B1 | 4/2008 | Herskowitz | |
| 7,857,803 B1 | 12/2010 | Salinas et al. | |
| 7,867,198 B2 | 1/2011 | Yamada et al. | |
| 7,879,020 B1 | 2/2011 | Salinas et al. | |
| 8,075,513 B2 | 12/2011 | Rudko et al. | |
| 8,157,785 B2 | 4/2012 | Salinas et al. | |
| 2005/0101907 A1 | 5/2005 | Sondeen | |
| 2010/0204649 A1 | 8/2010 | Miller et al. | |

OTHER PUBLICATIONS

Hoskins, SL et al. "Closed-Loop Resuscitation of Burn Shock" J Burn Care & Research (2006) 27:377-385.

Yamagushi M et al "An automated electronic anesthesia record and automated urine output measurement" Masui—Japanese Journal of Anesthesiology (2001) 50(2):210-3.

* cited by examiner

Closing Unit

Fluid Container Under Pressure

Release of Spent Fluid Container

Fluid Container Under Pressure

Emergency Pressure Release

Basic Infuser

Basic Infuser

Cross Section through Controller Area

Bolus Infuser

Bolus Infuser

Bolus Infuser

Bolus Infuser

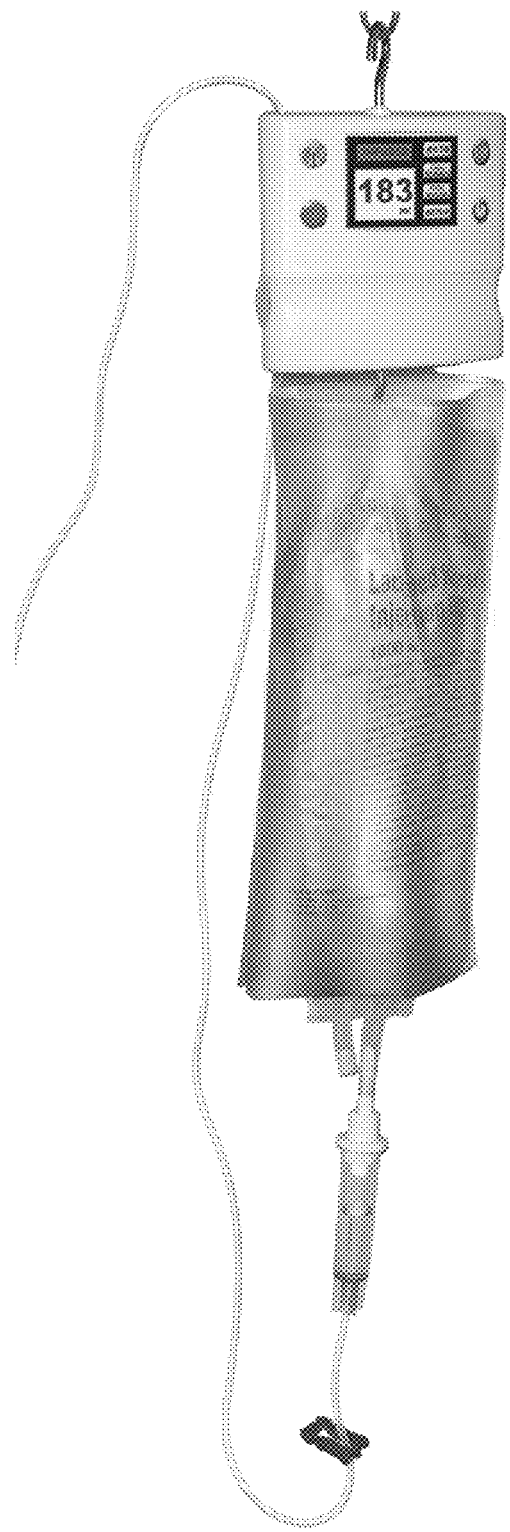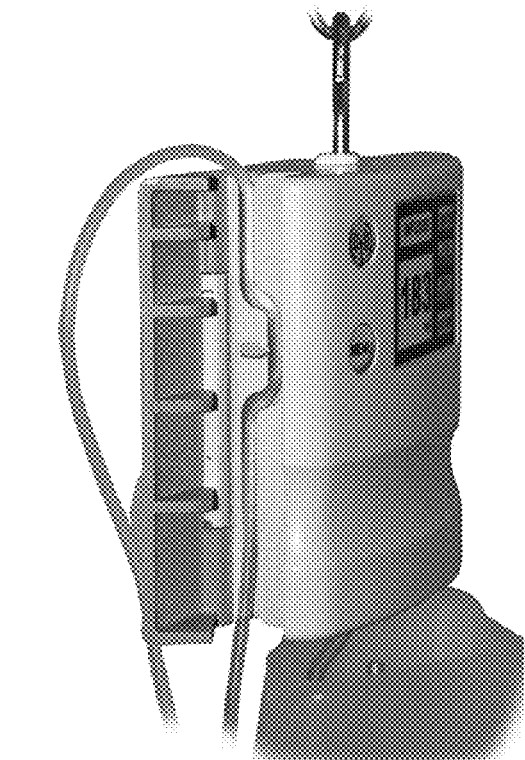
FIG. 9B
FIG. 9C
FIG. 9D

FLUID BALANCE MONITORING SYSTEM WITH FLUID INFUSION PUMP FOR MEDICAL TREATMENT

RELATED APPLICATIONS

This application claims the benefit of and priority to U.S. Provisional Patent Application Ser. No. 61/290,188, filed Dec. 26, 2009, incorporated by reference by the operation of closing paragraph of the specification, which operates to incorporate all references cited herein for their use according to applicable United States laws, rules and regulations.

GOVERNMENTAL RIGHTS

The government may have rights to certain subject matters disclosed herein pursuant to grant number N00014-03-1-0363 from the U.S. Government, Office of Naval Research.

BACKGROUND OF THE INVENTION

1. Field of the Invention

Embodiments of the present invention relate methods, systems, kits and apparatus in the field of medical treatment of patients needing bio-compatible fluids.

More specifically, embodiments of the present invention relate to methods, systems, kits and apparatus for treating patients needing the infusion of bio-compatible fluids, where the apparatus includes an assembly adapted to impart a desired pressure on a container containing a bio-compatible fluid for controlled and/or sustained fluid delivery to the patient.

2. Description of the Related Art

Patients injured by trauma, major surgery, burns, dehydration or hemorrhage, lose body fluid and often need bio-compatible fluids to remain alive. Patients with injuries causing hemorrhaging need volume expanders and blood transfusions; burn victims need electrolyte solutions or plasma protein solutions. The process of supplying the bio-compatible fluids to injured patients is known as "fluid therapy" in which the goal is to "resuscitate" a patient. Fluid therapy is often started by medics in pre-hospital care, but is sustained through care in the emergency department, operating room, and ICU until resuscitation is complete.

Severely injured patients need such fluids in critical amounts and at critical times in varying volumes and administered at various flow rates. The primary purpose of providing fluid is to restore loss of vascular volume (the patient's circulating blood volume). The primary means of administering fluid therapy is to infuse directly into the vascular space via an intravenous catheter or indirectly via an intraosseous catheter or oral intake. Too much fluid or too little fluid ("over-resuscitation" or "under-resuscitation" respectively) can increase patient morbidity and cause death. Further, the optimal rate and timing of providing the bio-compatible fluids varies, depending on the retention and loss of fluid in the vascular volume at different stages of resuscitation. Even further, the optimal volume and rate of fluid provided to the patient depends on the type of the injury such as a brain injury with hemorrhaging or penetrating abdominal injury. An excess or deficiency of total body fluid can occur when the administered fluid is out of balance with fluid losses due to urinary output, gastrointestinal losses, and hemorrhaging.

Typically, emergency personnel as first responders are minimally equipped to measure and determine appropriate amounts and rates of fluid provided to an injured patient. Other critical elements, such as drug delivery, airway maintenance, CPR for heart failure, compression of bleeding tissue, and other acute issues, take priority at the scene or during transit to an emergency room. Thus, emergency personnel often simply add one, two or more bags of fluid to a stand at an elevation higher than the patient and gravity feed the liquid. The volume and rates of fluid delivery are determined by intuition and hopefully experience of the emergency personnel. Fluid infusion rate is crudely controlled with a "thumb wheel" intravenous line occluder valve. In severe trauma, fluid infusion rate is often set "wide open" for rapid restoration of blood volume, but inattentiveness can result in excess fluid delivery. Thus, emergency personnel can easily vary widely from the fluid rate or volume that is optimally needed. It is known that under such circumstances, some patients develop morbidities or even expire due to over-resuscitation or under-resuscitation of the provided fluids. The scenario can be disastrous with a large number of patients suffering trauma such as in a mass transit crash, building collapse, or natural disaster. The limited attention to each patient can cause large discrepancies in the amounts of fluid needed to avoid over-resuscitation or under-resuscitation.

Air or gas pressurized bags can be placed around an intravenous (IV) fluid bag and inflated to a high pressure of typically 300 mm Hg to increase infusion rates when a patient needs a large volume of fluid fast. However, such high rates require even more concentration to monitor and optimally adjust.

An additional problem is the infusion of fluid into the circulation through intraosseous needles. Such intraosseous needles are placed in the bone marrow when veins are difficult to catheterize due to collapsed veins or short and narrow veins in children. The bone marrow provides a virtually uncollapsible vein with access to the circulation, but bone marrow has a low hydraulic conductivity (high resistance), which slows infusion rates. Thus, it would be desirable to have a high pressure infuser system that can deliver fluids from a bag at pressures of 600 mm Hg to 900 mm Hg or higher to achieve sufficient infusion rates when rapid resuscitation is required.

Even if the patient survives to a more fully equipped emergency room, the patient morbidity can increase significantly if the initial and ongoing treatment is inaccurate. One single period of low blood pressure in a patient with head injuries greatly increases that patient's morbidity and mortality. Low blood pressure can occur due to inadequate monitoring and fluid therapy. Fluid therapy for treatment of trauma and hemorrhage are often guided by monitoring a patient's arterial blood pressure, but continuous monitoring of blood pressure and rapid adjustment of infusion rate can be impractical due to other medical tasks required of care givers. This delay of care is exacerbated when multiple patients are present and particularly with mass casualty situations. Further, the data on the volume delivered to the patient can be critical in determining the subsequent fluid therapy.

Timely and accurate monitoring is needed to optimize patient outcomes. The transfer of the patient from the pre-hospital emergency medical team to the hospital emergency department can result in lost or erroneous data concerning the amount and timing of fluid actually delivered to the patient. This missed information can adversely affect the emergency department care-giver's judgment and treatment of the patient. Errors in patient records of fluid therapy can occur due to human errors of measurement and recording. Often fluid volumes infused and urine output produced are measured by visually inspecting IV fluid bags and urinary collection bags. Such an approach can lack accuracy and is intrinsically error prone. An automated system of better monitoring and control of fluid therapy would provide an advantage over the current methods of fluid therapy.

While the emergency room is generally better equipped than a first responder, the technology is still lacking to properly monitor and control the patient's resuscitation. In emergency departments, the volume of total fluid into the patient is typically manually recorded, and there is little data on infusion rates of fluid delivery.

Without displays of the tabular or graphical records of fluid therapy in relationship to clinical endpoints there is a danger of under-resuscitation or over-resuscitation.

Thus, emergency first responders have few tools suitable for the tasks that are critical to survival and generally use intuition and experience in controlling delivery of bio-compatible fluids. The typical large size of equipment and sophisticated controls found in hospitals equipment simply are not appropriate for pre-hospital first responders. These hospital units tend to be heavy and expensive and are relegated to AC power supplies with heavy battery backups. Most pre-hospital care givers do not have access to these units. Even the better equipped emergency rooms and hospitals are limited in the personnel and equipment to handle large scale disasters. Hospitals are also limited in their ability to monitor and optimally control administration of bio-compatible fluids.

Thus, there remains a need in the medical arts for a system, method and apparatus for better monitoring, control, and/or sustained delivery of fluid to a patient in need of bio-compatible fluids, the apparatus being suited for use in hospitals, mobile hospitals, emergency response vehicles, military medical response vehicles and/or field conditions.

SUMMARY OF THE INVENTION

Embodiments of the present invention provide an apparatus for delivery of a bio-compatible fluid to a patient, where the apparatus includes an openable housing adapted to receive a collapsible container containing the bio-compatible fluid (BCF), where the collapsible container or bag may be flexible or inflexible. The apparatus also includes a pressurization assembly for applying a constant and/or variable pressure across a portion of an outer surface of the bag to control a fluid delivery rate of the fluid as it leaves the bag through a delivery port in the bottom of the bag connected by a delivery tube to the patient. The pressurization assembly includes components to control the pressure applied to the bag and for rapid or controlled depressurization so that fluid delivery can be immediately stopped and reduced to gravity flow rate or controlled depressurization. The term rapid or rapidly means that the pressure in the pressurizing assembly or bladder assembly is reduced to ambient pressure within a short period of time, where a short period of time is a time less than 10 seconds. In other embodiments, rapid or rapidly means a time of less than 5 seconds. In other embodiments, rapid or rapidly means a time of less than 2.5 seconds. In other embodiments, rapid or rapidly means a time of less than 2 seconds. In other embodiments, rapid or rapidly means a time of less than 1.5 seconds. In other embodiments, rapid or rapidly means a time of less than 1 seconds.

Embodiments of the present invention provide an apparatus for delivery of a bio-compatible fluid to a patient, where the apparatus includes an openable housing adapted to receive a flexible bag containing a bio-compatible fluid (BCF). The apparatus also includes a pressurization assembly for applying a constant and/or variable pressure across a portion of an outer surface of the bag to control a fluid delivery rate of the fluid as it leaves the bag through a delivery port in the bottom of the bag connected by a delivery tube to the patient. The pressurization assembly includes components to control the pressure applied to the bag and for rapid depressurization so that rapid fluid delivery can be immediately stopped and reduced to gravity flow rate. The apparatus also includes a measuring or monitoring unit for measuring or monitoring a flow rate or a change in a weight of the bag on an intermittent basis, periodic basis, semi-continuous basis, continuous basis or any combination of intermittent, periodic, semi-continuous, or continuous bases.

Embodiments of the present invention provide an apparatus for delivery of a bio-compatible fluid to a patient, where the apparatus includes an openable housing adapted to receive a flexible bag containing a bio-compatible fluid (BCF). The apparatus also includes a pressurization assembly for applying a constant and/or variable pressure across a portion of an outer surface of the bag to control a fluid delivery rate of the fluid as it leaves the bag through a delivery port in the bottom of the bag connected by a delivery tube to the patient. The pressurization assembly includes components to control the pressure applied to the bag and for rapid depressurization so that fluid delivery can be immediately stopped and reduced to gravity flow rate. The apparatus also includes a measuring or monitoring component for measuring or monitoring a weight of the bag on an intermittent basis, periodic basis, semi-continuous basis, continuous basis or any combination of intermittent, periodic, semi-continuous, or continuous bases. The apparatus also includes a flow control unit for more accurate control of delivered fluid.

Embodiments of the present invention provide a portable trauma treatment system for delivering at least one bio-compatible fluid (BCF) from a portable fluid container to a patient, where the system includes a least one of the apparatus of this invention, one portable fluid container or a plurality of portable fluid containers, and a support structure for supporting at least one apparatus of this invention.

Embodiments of the present invention provide a portable trauma treatment kit for delivering at least one bio-compatible fluid (BCF) from a portable fluid container to a patient, where the kit includes an apparatus or a plurality of apparatuses of this invention, a portable fluid container or plurality of portable fluid containers, a support structure for supporting the apparatuses of this invention, auxiliary equipment, and a packaging structure of housing the kit components.

Embodiments of the present invention provide a portable treatment kit for delivering at least one bio-compatible fluid (BCF) from a portable fluid container to a patient, where the kit includes an apparatus or a plurality of apparatuses of this invention, a portable fluid container or plurality of portable fluid containers, a support structure for supporting the apparatuses of this invention, auxiliary equipment, which may include arterial blood pressure monitors (invasive or non-invasive), central venous pressure monitors (invasive or non-invasive), hemoglobin monitors, venous oxygen monitors, respiratory variability monitors, or similar monitors, a urinary output monitor, and a packaging structure of housing the kit components.

Embodiments of, the present invention provide a method of providing at least one bio-compatible fluid (BCF) to a patient comprising fitting a collapsible container including each BCF into an apparatus of this invention including a pressurization assembly. The method also includes pressurizing the container to a pressure sufficient to achieve a desired flow rate of delivered fluid from the container to the patient via intravenous or intraosseous catheters.

Embodiments of the present invention provide a method of providing at least one bio-compatible fluid (BCF) to a patient comprising fitting a collapsible container including each BCF into an apparatus of this invention including a pressurization assembly and a weight monitoring unit. The method also includes pressurizing the container to a pressure sufficient to achieve a desired flow rate of delivered fluid from the container to the patient. The method also includes monitoring a weight of the container to determine the volume of fluid delivered to the patient.

Embodiments of the present invention provide a method of precisely measuring volume in a fluid bag or container using one or more scales or load cells and/or one or more accelerometers with data processing and analysis of load cells and/or accelerometers using signal filtering, Bayesian and statistical analysis, classifiers, or other similar methods for accurate measuring of fluid volume in a container.

Embodiments of the present invention provide a method of providing at least one bio-compatible fluid (BCF) to a patient comprising fitting a collapsible container including each BCF into an apparatus of this invention including a pressurization assembly, a weight monitoring unit and flow control unit. The method also includes pressurizing the container to a pressure sufficient to achieve a desired flow rate of delivered fluid from the container to the patient. The method also includes monitoring a weight of the container to determine the volume of fluid delivered to the patient. The method also includes the step of controlling the flow rate of delivered fluid from the container to the patient.

Embodiments of the methods of this invention can also include the step of changing the pressure at one time, intermittently, periodically, semi-continuously, continuously or any combination of intermittently, periodically, semi-continuously, or continuously changing the pressure applied to the container so that the flow rate of fluid can be changed accordingly. In this way, fluid delivery protocols can be delivered to patients according to a pre-programmed fluid delivery protocol, according to a protocol established by a practitioner at the time or according to a protocol communicated to the apparatus remotely via wired or wireless communication hardware and software.

Embodiments of the methods of this invention can also include the step of changing the pressure at one time, intermittently, periodically, semi-continuously, continuously or any combination of intermittently, periodically, semi-continuously, or continuously changing the pressure applied to the container so that the flow rate of fluid can be changed accordingly, where fluids and the fluid flow rate are controlled by a decision assist or autonomous closed loop controller with infusion rate set by an algorithm based on input such as blood pressure, urinary output, other physiological variables, derivatives thereof or mixtures or combinations thereof.

Embodiments also relate to kits or systems as set forth above also including infusion devices, IV pumps, urinary output monitors, vital signs monitors, decision assist or autonomous controllers or mixtures or combinations thereof.

BRIEF DESCRIPTION OF THE DRAWINGS

The invention can be better understood with reference to the following detailed description together with the appended illustrative drawings in which like elements are numbered the same:

FIGS. 9B-D depict 3D renderings of a particular commercial embodiment of the apparatus of FIG. 9A.

DETAILED DESCRIPTION OF THE INVENTION

Figure 1A:
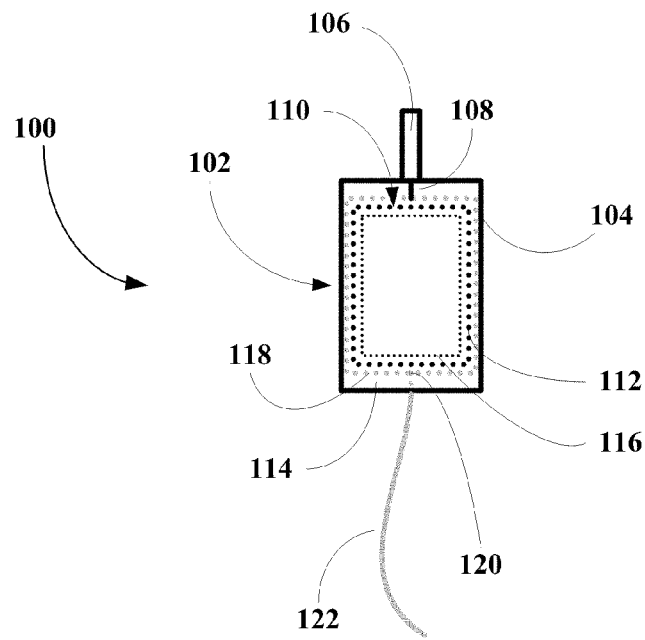
FIG. 1A depicts an embodiment of an apparatus of this invention including a pressurization assembly.

The inventors have developed unique apparatus, kits, systems and methods for the delivery of a bio-compatible fluid to a patient such as an animal including an human. The inventors designed a portable apparatus including a housing having a door pivotally mounted thereon to receive a collapsible container including a bio-compatible fluid. The portable apparatus includes a pressurization assembly for applying a pressure to the container to produce and control a flow rate of fluid being delivered to the patient or conversely to control a flow rate of fluid leaving the container. The inventors have also found that the apparatus can be equipped with a weight measuring and monitoring unit for measuring and monitoring fluid volume delivery and flow rates and to generate output signals associated with events such as container replacement notices, volume delivery notices, etc. The inventors have also found that the apparatus can be equipped with a flow control unit to improve control of the rate of fluid delivery to the patient and precisely set flow rate. The inventors have found that one of the features of the apparatus of this invention is the ability to quickly change IV bags after dispensing. Current devices require a slow exhaust of the air in the bladder to get the old bag out and complete evacuation of the bladder before inserting a new IV bag. In the present invention, we accomplish faster change by rapid exhaust of the air in the bladder and an easily opened door which latches securely when under pressure.

Embodiments of the present invention broadly relate to an apparatus for delivering a fluid to a patient, where the apparatus includes a pressurizing assembly, and where the pressurizing assembly surrounds all or a portion of a bio-compatible fluid container. By pressurizing the pressurizing assembly via a pressurization assembly so that a controlled force may be exerted on the container surrounded in whole or part by the pressurizing assembly, a flow rate of the bio-compatible fluid exiting the container and flowing to a patient is in turn controlled.

Embodiments of the present invention broadly relate to an apparatus for delivering a fluid to a patient, where the apparatus includes a bladder assembly, and where the bladder assembly comprises a bladder and sleeve. The bladder and sleeve may be an integral unit or two separate components. Whether unitary or non-unitary, a front outer surface of the bladder and an inner surface of the sleeve are designed to engage a bio-compatible fluid container so that a controlled force may be exerted on the container, which in turn controls a flow rate of the bio-compatible fluid exiting the container and flowing to a patient. Thus, the bladder assembly forms a pocket into which the container is placed so that the container wall contacts the front outer surface of the bladder and an inner surface of the sleeve. As the bladder is inflated, the bladder and sleeve cooperate to exert a controlled force on the container. This controlled force translates into a controlled flow of fluid from the container.

Embodiments of the present invention broadly relate to an apparatus for delivery a fluid to a patient, where the apparatus includes a housing having a door pivotally mounted onto the housing so that the door can transition between a closed state and an opened state. The housing and door have an exterior cross-sectional profile and an interior cross-sectional profile, that can be the same, similar or different. When the door is in its closed state, the housing and door form a longitudinally extending cavity having an internal cross-sectional profile contoured to accommodate a collapsible bio-fluid container, such as an IV bag, placed inside the apparatus. The housing and the door include mutually interlocking detachable connectors so that the door can be detachably locked in its closed state. The housing includes an attaching member such as a hanging member, extending from its outer top surface so that the apparatus can be attached to or hung from a support structure, which in certain embodiments is a specifically designed structure. The housing also includes a holding member disposed on an inner surface of the housing adapted to hold a flexible container containing the bio-compatible fluid (BCF), such as an IV bag.

The housing also includes a pressurization assembly including a pressurizable member disposed in, on or against the inner surface of the housing below the holding member. The housing also includes an aperture through its inner surface. The pressurization assembly also includes a pressurization unit mounted on an outer back surface of the housing. The pressurization unit includes an air pump, a tube connecting the pump to that pressurizable member and passing through the aperture, a pump control unit and a battery unit, where the pressurization unit is adapted to change an internal pressure of the pressurizable member. The internal pressure of the pressurizable member can be changed to a desired or set point pressure, can be intermittently set to one or more desired pressures, can be periodically varied, can be semi-continuously varied, can be continuously varied or the pressure can be changed using a combination of any of these change protocols. The pressurization unit also includes a rapid pressure relief valve that when activated, will work to immediately depressurize the pressurizable member. When the apparatus includes a BCF container disposed therein and the pressurizable member is pressurized, the pressurizable member will push against the container increasing a fluid flow rate out of the container. By increasing or decreasing the pressure, one can conveniently and effectively change the fluid flow rate.

Embodiments of the present invention may provide an apparatus including a weight measuring and monitoring unit. The weight measuring and monitoring (WMM) unit includes a connector for detachably connecting the pressurization assembly described above. The WMM unit also includes a means for measuring the weight of the pressurization assembly and thereby monitoring and measuring the volume of fluid delivered based on the density of bio-compatible fluid. The volume of fluid delivered can be used to alert practitioners of remaining container volume, volume delivered, etc. An apparatus of this invention including a WMM can be designed so that the entire apparatus is a unitary structure.

Embodiments of the present invention may provide an apparatus including a fluid flow control (FFC) unit. The FFC unit includes a flow control valve through which the fluid flows out of the BCF container. The valve is controlled by flow control circuitry to regulate the flow rate of fluid through the valve, thus, permitting improved flow control of fluid being delivered to a patient. Embodiments of this invention can of course also include both a WMM unit and an FFC unit.

Embodiments of the pressurizable member of this invention can comprise a bladder composed of a viscoelastic material. In certain embodiments, the bladder is a closed form having an opening through which a gas, for example air, can be pumped in or exhausted from the bladder. In other embodiments, the bladder is a sheet of a viscoelastic material, where its edges are rounded and are designed to be pressed into a receiving groove formed in the inner surface of the housing forming a cavity for rounded edges of the bladder sheet. Gas is introduced and exhausted through the aperture in the housing. In certain embodiments, the bladder extends from a position just below the holding member to a position just above a bottom of the housing or extends over substantially the entire length of the cavity. In other embodiments, the bladder extends over a middle portion of the interior surface of the housing or extends over a smaller portion of the cavity.

Suitable bio-compatible fluids (BCF) for use in this invention include, but are not limited to any fluid that can be given to a patient, where the fluid is designed to be given to the patient in a controlled manner. Examples include, without limitation, electrolyte solutions commonly known as "crystalloids", plasma, artificial plasma commonly known as "colloids", blood, blood products, other fluids that can be provided internally to a body for therapeutic or medical purposes, bio-compatible fluid including pharmaceuticals, nutriceuticals, or other compounds designed to produce a therapeutic effect on the patient.

Embodiments of the present invention are portable, lightweight system suitable for civilian prehospital and military field use. The systems all incorporate an apparatus including a housing and a pressurization subsystem, where the apparatus is adapted to hold a BCF container and the pressurization subsystem is adapted to apply a force to the container to change a flow rate of fluid from the container to a patient. The systems can also include a weight monitoring and measuring subsystem and/or flow rate monitoring subsystem and/or a fluid flow control subsystem. The systems can also include control hardware and software to measure fluid flow, to control fluid flow, to display fluid flow rates and fluid delivery volumes, to notify practitioners of events, etc. The hardware and software can also include communication (wired or wireless) hardware and software to transmit data to an off-site location or locations. The systems of this invention are designed to operation with the aid of one or more microprocessors designed to measure fluid flow rates and fluid delivery volumes, to control fluid flow rates, to alert practitioners of desired events, etc.

It should be recognized that the various apparatus of this invention may require calibration of specific components to ensure desired fluid delivery and fluid delivery monitoring.

The various apparatus of this invention can be economically constructed to be used with off-the-self IV fluid components and made of inexpensive components, including standard IV bags, IV pressure bags, infusion sets, catheters, or the like. The apparatus are simple, inexpensive, and novel systems that provide accurate and controlled fluid infusion rates for use in the field and/or emergency situations to assist medical personnel in resuscitation of burns and hemorrhage and other treatments. Such apparatus may be used in prehospital environments, field environments, enroute environments (field, ambulance, life-flight, Casevac and Medevac), operating room environments, intensive care units, and hospital wards or for home health care for fluid delivery including drugs or other pharmaceutical compounds.

Indices of the adequacy of fluid therapy are blood pressure or urinary output. The rationale for urinary output monitoring is that if it is adequate, then glomerular filtration rate and renal blood flow are adequate, which in turn implies that cardiac output and blood volume are adequate for normal tissue perfusion. If a patient's blood pressure or urinary output are below a clinically desirable target, then the patient needs more fluid; if blood pressure or urinary is higher than targets, then the fluid infusion rate and volume delivered can be decreased. Current fluid therapy devices are manual IV drips and IV pumps. Neither of these devices has displays that facilitate the prevention of under-resuscitation or over-resuscitation. They provide limited displays of infused rate, volume infused and volume to be infused. These displays are separate and removed from the displays of blood pressure and urinary output the key variables that fluid therapy is performed to alter.

Having described the overall embodiments which may be used in a variety of combinations with each other and with other variations in fluid therapy, attention is turned to specific examples of combinations. It is understood that such embodiments are merely exemplary as the invention can comprise various other elements used in combination with each other to provide the system functions described herein.

Fluid Monitors

Several fluid monitors are described herein as a means to measure the volume of fluid delivered from a fluid container to a patient and to control the rate at which fluid is delivered from the fluid container to a patient. One embodiment of such an apparatus includes a housing, a bladder and a pump adapted to pressurized a flexible fluid container as the driving force for fluid outflow from a fluid container such as an IV bag properly positioned within the bag. The apparatus can also include a pressure sensor for taking pressure readings on an intermittent basis, a periodic basis, a semi-continuous basis, substantially continuous basis, and/or continuous basis. The apparatus can also include a processing unit, where the processing unit receives sensor input from the pressure sensor and adjusts pump speed to maintain a desired fluid flow rate. The processing unit can also be calibrated for pressure difference ($\Delta P$) versus volume difference ($\Delta V$) to automatically adjust fluid flow based on the fluid volume remaining in the fluid container. A processing unit or controller may be actuated to control the pressure exerted on the fluid container and thus, the fluid flow rate out of the fluid container. Additionally, the apparatus can include a flow control unit such as a linear actuator (e.g., solenoid actuator) pinch valve on an outflow fluid tubing in order to increase or decrease a net flow rate and control fluid flow from the fluid container. The processing unit (generally a microprocessor) can adjust the duty cycle of the control unit (ratio of open/close time) to achieve a desired flow rate or a flow rate profile manually set or automatically set by the processing unit. This type of flow control unit provides a simple (one primary moving part), lightweight and inexpensive virtual pump or "pump" as defined herein. Another type of flow control unit can include a stepper motor, which provides a variable clamp on the tubing to provide finer control of fluid than a linear actuator (e.g., solenoid) valve, so that the infusion rate is controlled by changing a flow resistance through the tubing connected between the outlet port of the fluid container and a patient. This fine control can be used to achieve a constant or substantially constant flow rate from the apparatus to the patient.

In another embodiment of the apparatus of this invention, the apparatus can include, in addition to or instead of the flow control unit, an electronic scale (e.g., a load cell, a force transducer, or similar device), from which the fluid container such as an IV bag hangs. The scale allows calculation of a fluid volume change ($\Delta V$) based on a change in fluid weight ($\Delta W$) and the fluid's specific gravity. The fluid delivery systems may be adjusted/programmed to compensate for different fluid specific gravities and calculate volume and flow rates.

A second weight scale below the IV bag can assist in accuracy of the apparatus. The second scale can correct for any weight or supporting forces of the tubing and forces below the fluid container generated by tubing, flow controller, or such.

Accelerometers on load cells above and/or below the IV bag provide further data that can be processed to further improve accuracy of volume and calculated flow by correcting for motion artifacts, which are especially prevalent during en route care.

Any of these fluid delivery systems can be interfaced with a processing unit, such as a local microprocessor or a remote processor, that measures time, determines bag volume of the fluid container by a variety of methods described, then calculates flow. The apparatus also include a source of electrical energy or power for supply power to the processing unit, the pump, the optional scale and the optional flow control unit. The apparatus of this invention can include an ON/OFF switch, an indicator light, and a pressure relief valve.

Displays

Any of these fluid delivery systems can have a display that provides infusion rate, infused volume and volume to be infused. In order to provide the care giver with more information on fluid balance a graphical or tabular record of the time course of fluid delivered could be displayed. Further, these fluid delivery systems can communicate directly or indirectly through a central hub to a vital signs monitor, urine output monitor, and/or electronic medical record, thus, allowing graphics on fluid delivery to be combined with graphical displays or tabular displays of resuscitation endpoints such as urinary output or blood pressure both at bedside and in the patient medical record. The coupling of data from the fluid delivery system and resuscitation endpoints further assists in reduction of errors of over-resuscitation and under-resuscitation.

The processing unit can be connected directly to the container or can include a decision assist or closed loop controller, possibly utilizing a microprocessor, which can connect to a urinary output monitor or vital signs monitor or other physiologic monitor or record-keeping system or a mixture or combination thereof.

Pumps

Suitable pumps for use in the various apparatus of this invention include, without limitation, any positive displacement pump or rotodynamic pump, or combinations thereof. Exemplary examples include, without limitation, diaphragm pumps, piston pumps, oscillating pumps, gear pumps, progressive cavity pumps, roots-type pumps, peristaltic pumps, reciprocating-type pumps, centrifugal pumps, radial flow pumps, axial flow pumps, mixed flow pumps, eductor-jet pumps, any other type of pump, or combination thereof. The pumps are designed to pressurize a bladder disposed in an interior of a housing, where the housing is designed to receive a fluid container. As the bladder is pressurized by a gas such as air pumped into it by the pump, the bladder expands exerting a force on the fluid container. Increasing the pressure within the bladder, increases the force on the fluid container enclosed within the housing. As the fluid container is collapsible, the force is transmitted to the fluid within. As pressure within the fluid container is increased, the rate of fluid flow out of the container increases. Thus, by controlling the pressure in the bladder using the pump, we can control the rate of fluid flowing out of the container. Again, the processing unit can include protocols to adjust the bladder pressure so that fluid flow rate out of the container remains substantially constant or the processing unit can include protocols to change the pressure on the bladder and thereby change the flow rate out of the container in a desired flow rate profile or a flow rate protocol or flow rate profile may be entered into the processing unit by a manual interface or by a wired or wireless interface from a remote or external computer.

DETAILED DESCRIPTION OF THE DRAWINGS

Referring now to FIG. 1A, an embodiment of a portable fluid delivery system of this application, generally 100, is shown to include a portable fluid delivery (PFD) unit 102. The PFD unit 102 includes an openable housing 104 having a housing hanging member 106 and a bag hanging member 108. The housing 104 includes a pressurization assembly 110. The pressurization assembly 110 includes a bladder 112 disposed in an interior 114 of the housing 104 and a pressurization unit 116 disposed on a back exterior surface (not shown) of the housing 104. Disposed within the housing 104 is a collapsible bio-compatible fluid container 118 hung in the interior 114 of the housing 108 via the bag hanging member 108. The container 118 includes an outlet port 120 connected to a fluid conduit 122. The PFD unit 102 is adapted to apply a pressure onto a portion of the container 118 producing a desired rate of fluid delivery (i.e., fluid flow rate) out of the container 118 through the port 120 and into the conduit 122, which is connected to a catheter or other device for introducing fluids into the circulatory system of an animal including a human.

Figure 1B:
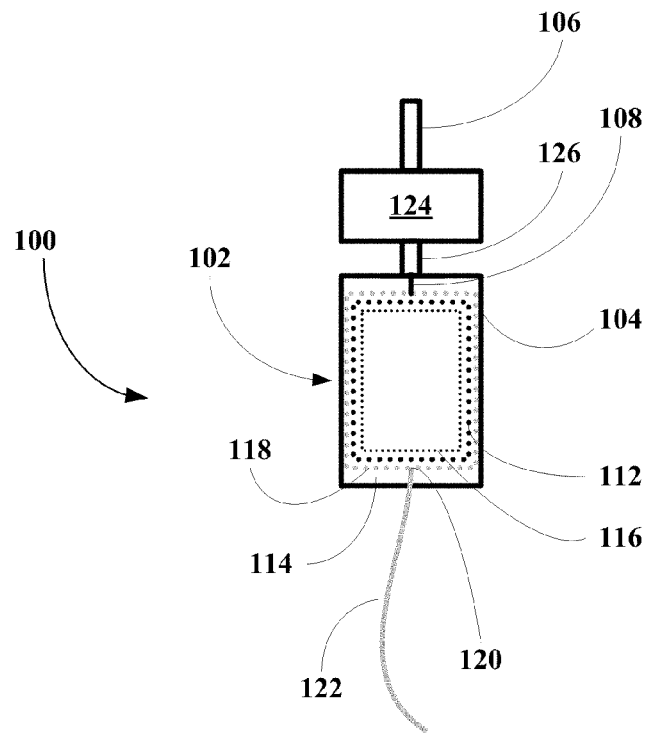
FIG. 1B depicts an embodiment of an apparatus of this invention including a pressurization assembly and a weighing assembly.

Referring now to FIG. 1B, another embodiment of a portable fluid delivery system of this application, generally 100, is shown to further include a weight measuring and/or monitoring (WMM) unit 124. The PFD unit 102 is connected to the WMM unit 124 by a connection member 126 that connects the WMM unit 124 to the PFD unit 102. The weight measuring and/or monitoring unit 124 is adapted to measure and/or monitor the weight to the container 118 or the PFD unit 102 depending on the configuration of the WMM unit 124. The infusion monitor or WMM unit 124 is adapted to monitor a fluid delivery rate of BCF to the patient through the conduit 122.

Figure 1C:
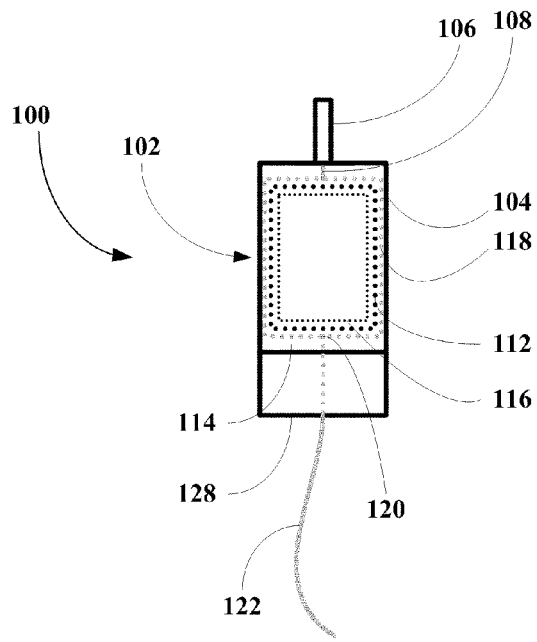
FIG. 1C depicts an embodiment of an apparatus of this invention including a pressurization assembly and a flow control assembly.

Referring now to FIG. 1C, an embodiment of a portable fluid delivery system of this application, generally 100, is shown to further include a fluid flow control (FFC) unit 128, where the fluid flow control unit 128 is adapted to control the rate of fluid flow into the conduit 122 by allowing the fluid to flow unrestricted or restricting flow into the conduit 122 to control the rate.

Figure 1D:
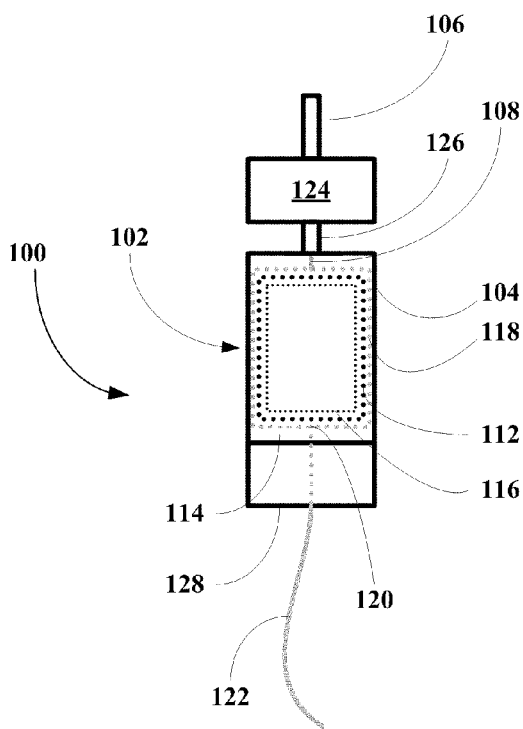
FIG. 1D depicts an embodiment of an apparatus of this invention including a pressurization assembly, a weighing assembly and a flow control assembly.
Figure 1E:
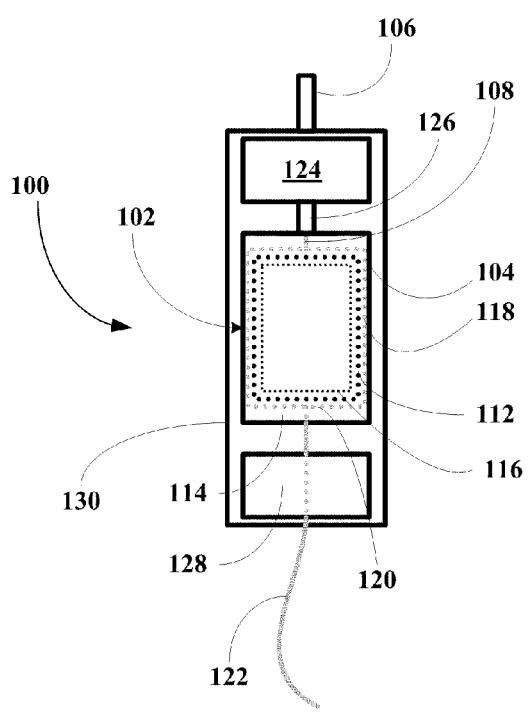
FIG. 1E depicts an embodiment of an apparatus of this invention including a pressurization assembly, a weighing assembly and a flow control assembly, within a housing.

Referring now to FIG. 1D, an embodiment of a portable fluid delivery system of this application, generally 100, is shown to further include the weight measuring and/or monitoring (WMM) unit 124 and the fluid flow control (FFC) unit 128. In certain embodiments as shown in FIG. 1E, the entire assembly including the fluid delivery apparatus 102, the WMM unit 124 and the FFC unit 128 can be included in a single structure 130. Of course, it should be recognized that the embodiments of FIGS. 1B and 1C can also be housed within an opened or closed, yet openable structure. It should also be recognized that all of the apparatuses of FIGS. 1A-E can be attached via housing hanging connector 106 to any support or can simply be placed on a surface provided that the conduit 122 is not pinched or otherwise constricted.

Embodiment for pressurized system also includes apparatus that do not need to hang or be hung, but include a flow controller to control and regulate flow. The apparatus can be used by being set to deliver a timed dose or volume of fluid at a high flow rate. With such an apparatus the timed flow rate can be calculated using the measured and calibrated pressure-flow relationship of the IV tubing and vascular catheter or intraosseous needle size being used. The calculation is also based on knowing the fluid bag driving pressure e.g. 300 mm Hg, the height of the fluid bag above the catheter insertion and an estimate of the effective catheter exit pressure (between 2 and 15 mmHg for intravenous infusion), as disclosed below.

Alternatively, the flow may be calculated independently of the catheter size and position of any occlusion valve by measuring the pressure proximally upstream of the catheter and any occlusion valve, knowing the fluid bag driving pressure and height of the fluid bag above the pressure measurement site, and applying the calibrated pressure-flow relationship of the intervening tubing, as disclosed below.

Furthermore, in the previous embodiment, the hydrostatic height of the fluid bag may be calculated whenever the occlusion valve is closed to flow, from the pressure measured at the aforementioned site proximally upstream of said occlusion valve, as disclosed below.

Figure 1F:
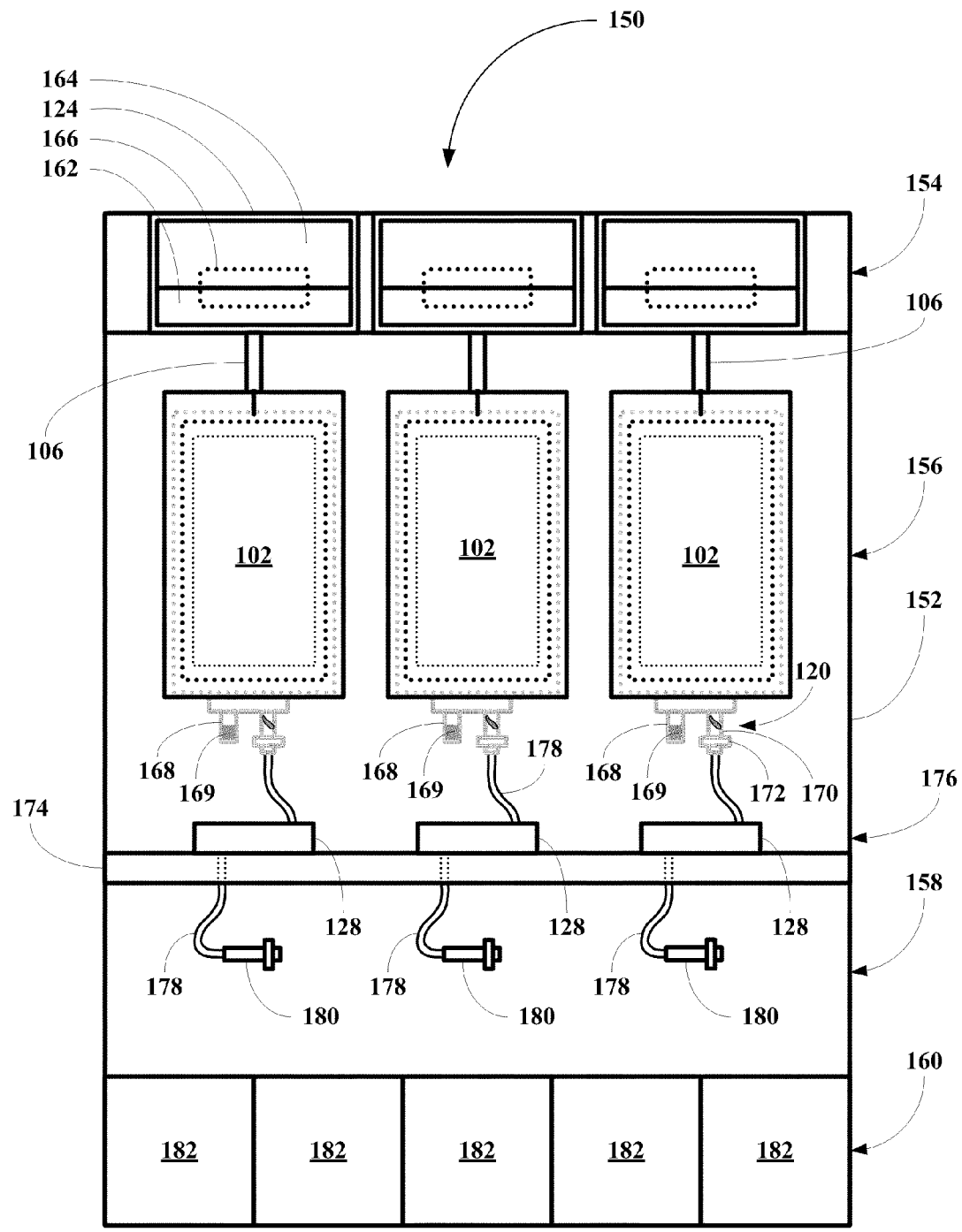
FIG. 1F depicts an embodiment of a kit including a housing and a plurality of the apparatuses of FIG. 1E.

Referring now to FIG. 1F, an embodiment of a portable fluid delivery kit of this invention, generally 150, is shown to include a support structure 152 comprising a portable box, container or similar portable structure. The kit 150 includes a top section 154, a PFD section 156, a transfer section 158 and a lower section 160. The top section 154 includes a plurality of weight measuring and/or monitoring (WMM) units 124, here three, but the support structure 152 can be designed to accommodate from 1 to up to 5 or more WMM units 124. Each WMM unit 124 includes a control panel 162, a display 164 and a processing unit 166. The control panel 162 permits manual or remote control of the WMM 124 and its associated PFD 102 and FFC unit 128. The PFD section 156 includes the associated PFD units 102 connected to their respective WMM units 124 by the housing hanging member 106. Each BCF container 118 (see FIGS. 1A-E) includes a med port 168 with a septum 169 and the outlet port 120 comprising a drip unit 170 and a fitting 172. The support structure 152 includes a platform 174 at a bottom 176 of the PFD section 156 upon which is situated the corresponding FFC units 128 for each PFD 102. Each FFC unit 128 includes a tubing 178 that connects to the fitting 172, passing through the FFC unit 128 as explained below and then passing through the platform 174 and extending into the transfer section 158 ending in a fitting 180. The lower section 160 includes a plurality of compartments 182 that can hold BCF containers, tubing, catheter, or other items that a medical practitioner may need in the field or in an emergency vehicle.

Figure 2A:
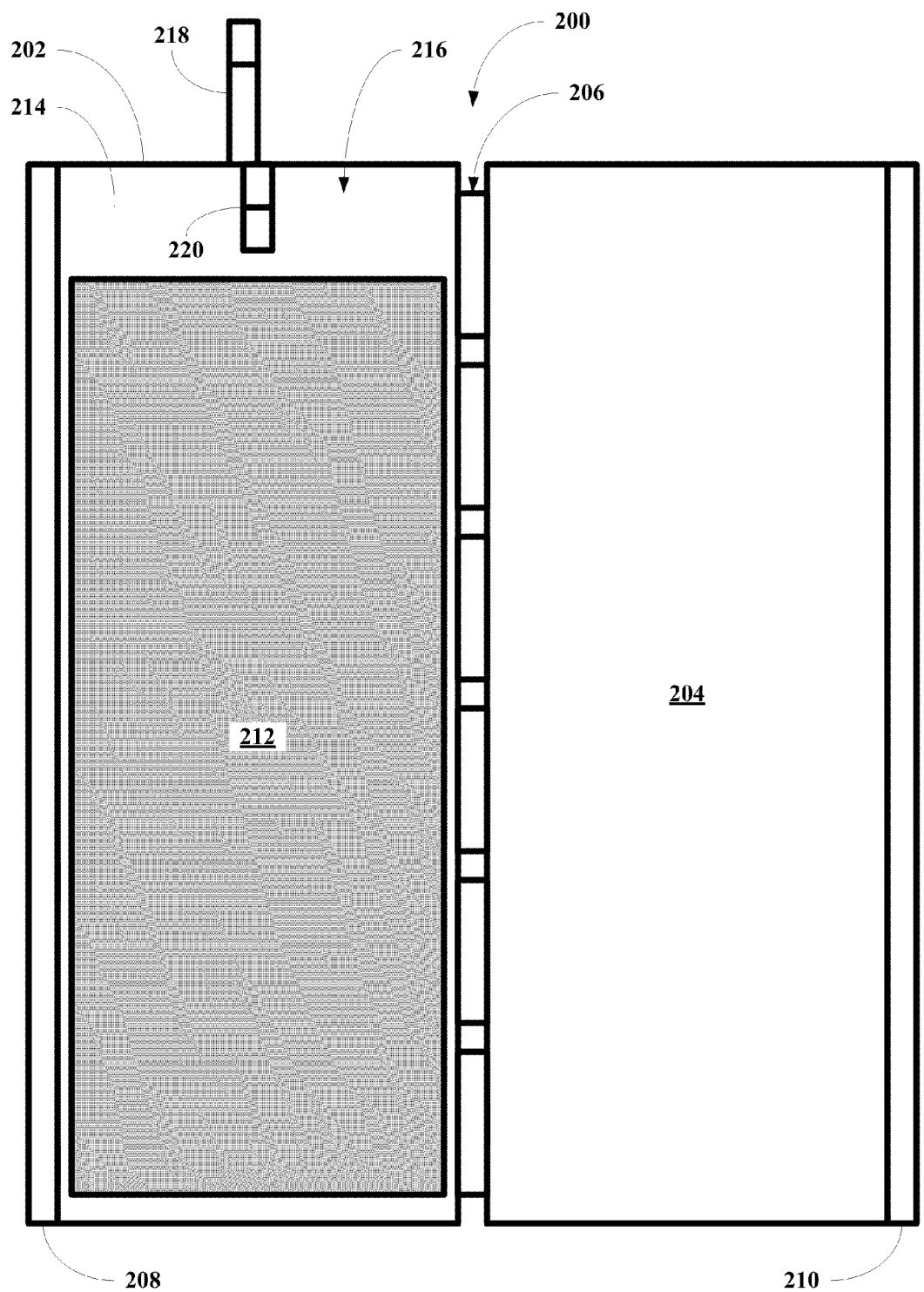
FIG. 2A depicts an embodiment of a plan view of a pressurization assembly of this invention shown in an opened state.

Referring now to FIG. 2A, an embodiment of the PFD unit, generally 200, is shown in its opened state to include a housing 202 including a door 204 pivotally mounted to the housing 202 via a hinge 206. The housing 202 includes a first connector 208 adapted to detachably and optionally lockingly engage a second connector 210 on the door 204 so that the door 204 can be opened and closed and optionally locked in its closed state. The unit 200 also includes a bladder 212 disposed against an inner surface 214 of an interior 216 of the housing 202. The housing 202 also optionally includes a unit hanging connector 218 and a bio-compatible fluid container hanging connector 220. The connector 218 is adapted to hang the unit 200 from any support structure (not shown). The connector 220 is adapted to support a bio-compatible fluid container (not shown).

Figure 2B:
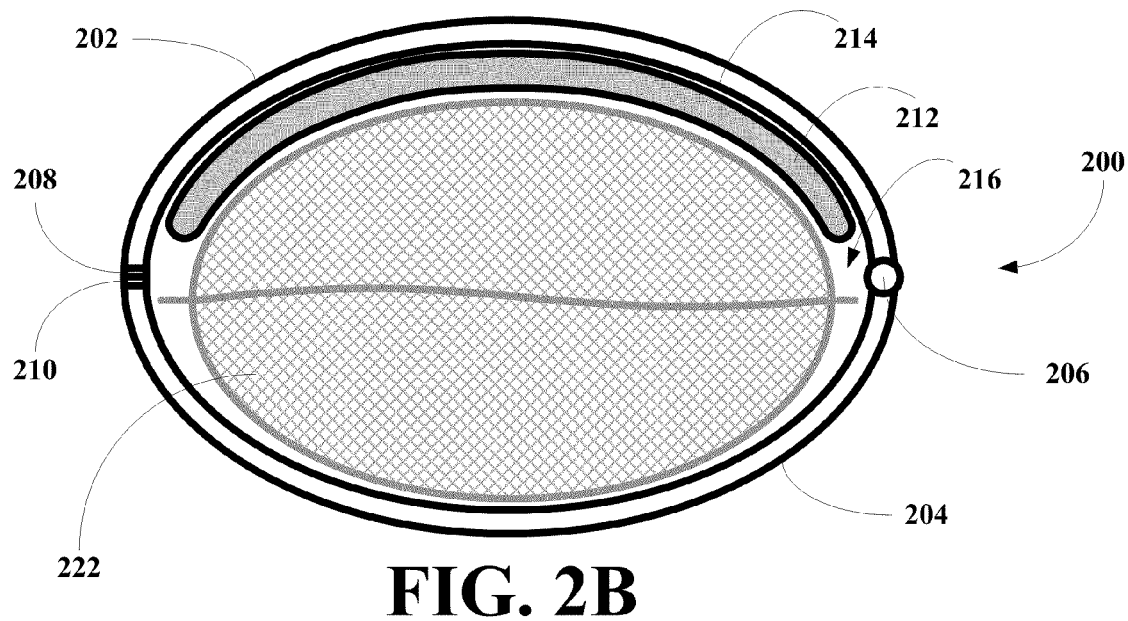
FIG. 2B depicts a cross-sectional view of the pressurization assembly of FIG. 2A, but shown in a closed state.

Referring now to FIG. 2B, a cross-sectional view of an embodiment of the PFD unit 200 is shown in its closed state with a bio-compatible fluid container 222 disposed within the housing 202. The bladder 212 is shown deflated conforming to an outer surface of the container 222.

Figure 2C:
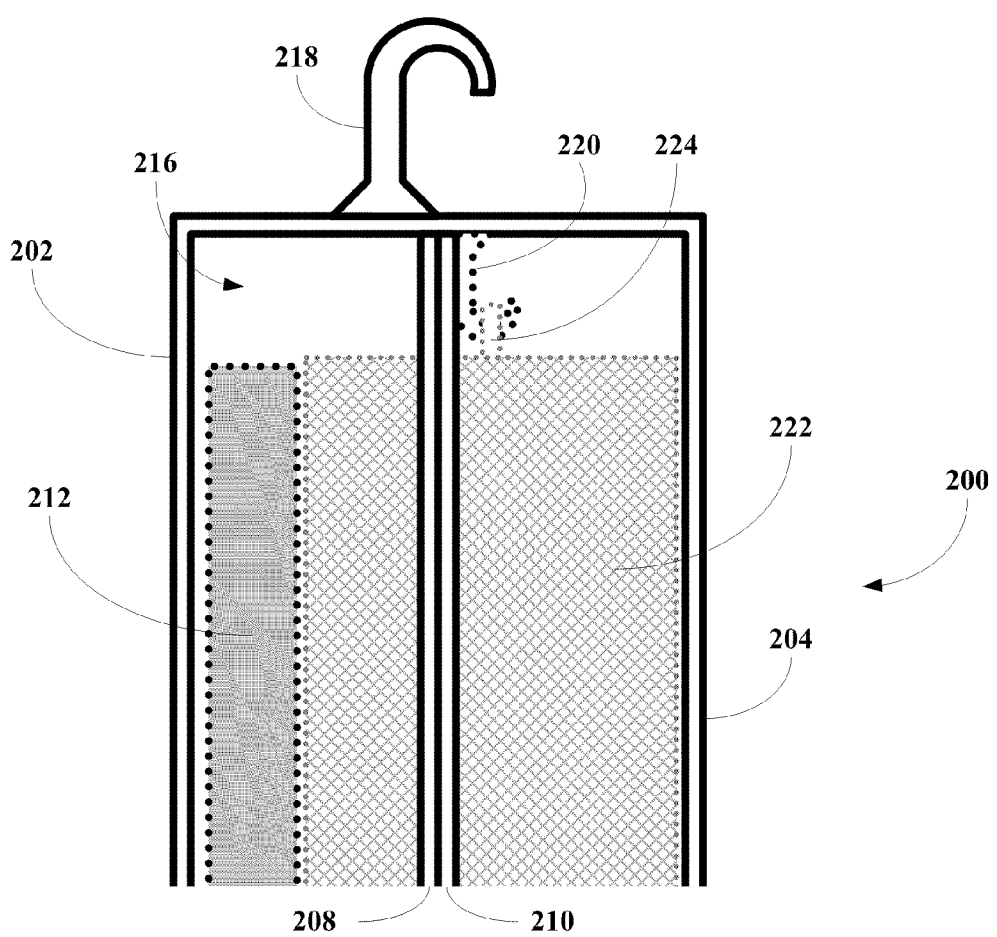
FIG. 2C depicts a partial side view of the pressurization assembly of FIG. 2A, but shown in a closed state.

Referring now to FIG. 2C, a side view of an embodiment of the PFD unit 200 is shown in its closed state with a bio-compatible fluid container 222 disposed within the housing 202 and hanging from the connector 220. The connector 220 is shown here as a hook and the container 222 is hung via an aperture (not shown) in a top tab portion 224 of the container 222. In this embodiment, the unit connector 218 is shown also shown as a hook. Of course, the container connector 220 can be any connector that permits the container 222 to be disposed in the interior 216 of the unit 202 and the unit connector 218 can be any connector that can be used to mount or hang the unit 200 from a support structure (not shown) including hooks as shown here, magnets, hook and loop, straps, belts, bolts, or the like or combinations thereof.

Figure 2D:
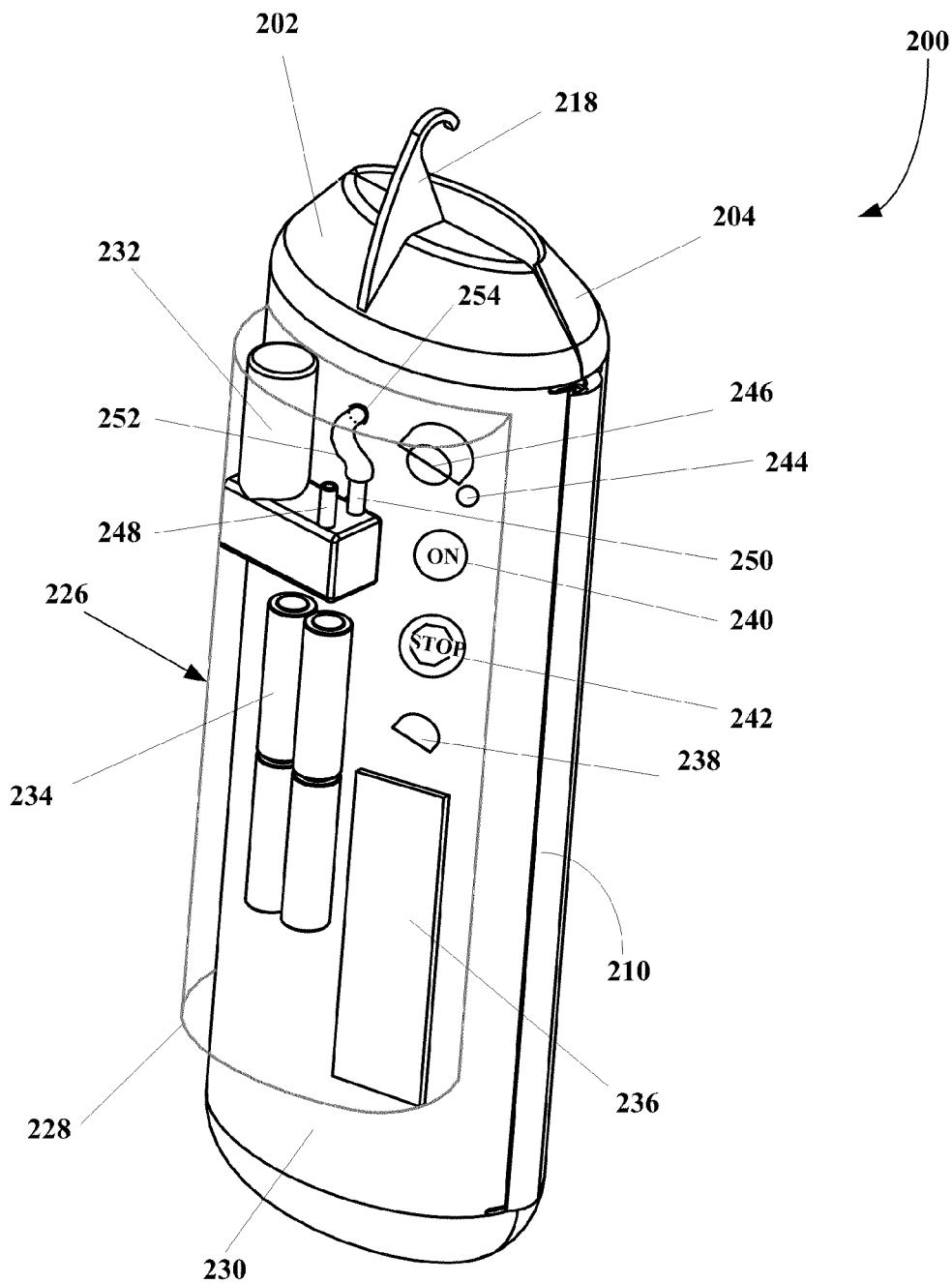
FIG. 2D depicts an embodiment of a pressurization assembly of this invention.

Referring now to FIG. 2D, a perspective rear view of and embodiment of the PFD unit 200 is shown to include a pressurization unit 226. The pressurization unit 226 includes a cover 228, which can be pivotally mounted to a back outer surface 230 of the housing 202 via a hinge (not shown) or can snap in place using snap connectors (not shown). The unit 226 also includes a pump 232, a power supply 234, a controller 236, a pressure sensor 238, an ON button 240, an OFF button 242, an indicator light 244 and a rapid exhaust valve 246. These components are either mounted directly onto the back exterior surface 230 of the housing 202 or are mounted on a separate member that is mounted to the back exterior surface 230 of the housing 202. The pump 232 includes an inlet 248 and an outlet 250. The pump outlet 250 is connected via a hose 252 extending through an aperture 254 in the back (not shown) of the housing 202 to an inflation port (not shown) of the bladder 212.

Figure 3A:
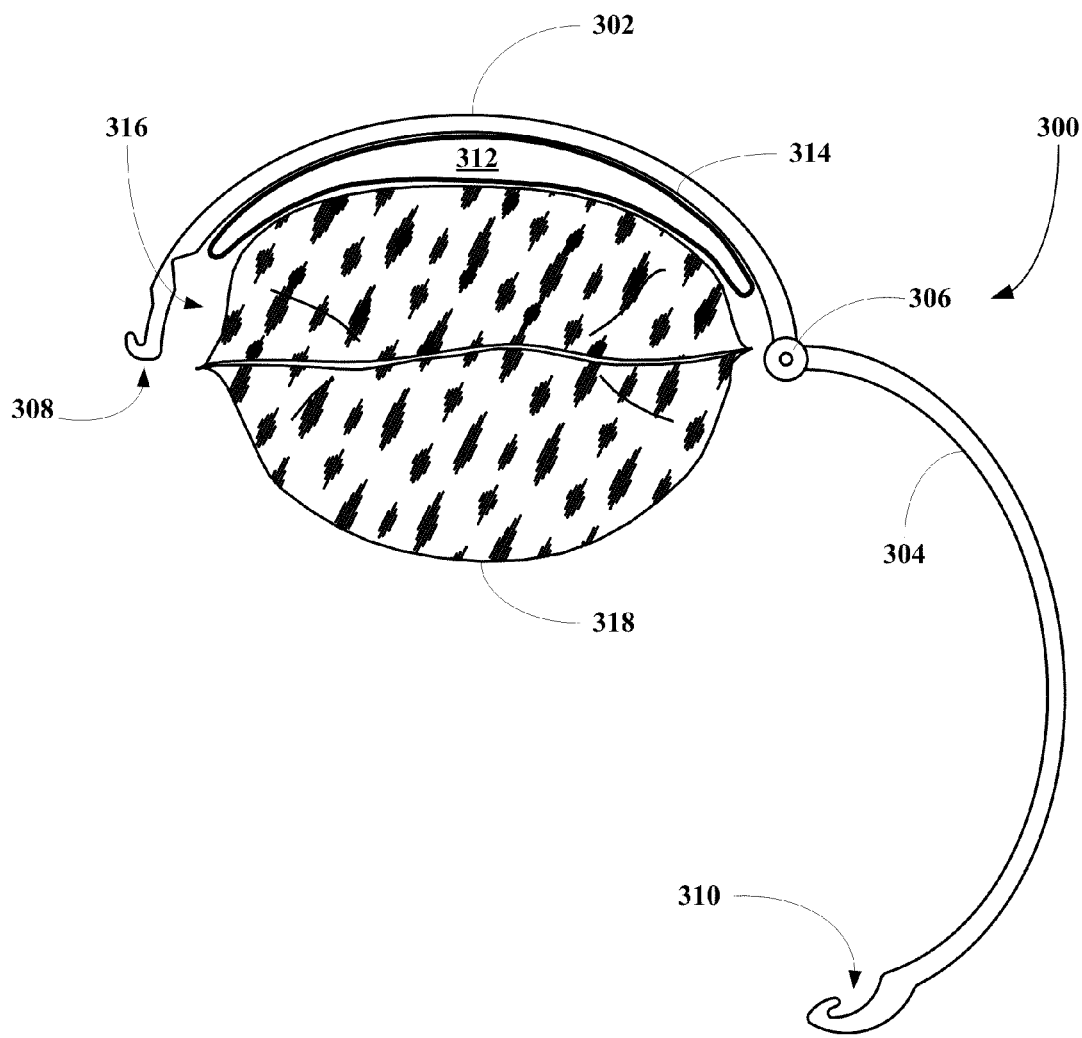
FIG. 3A depicts an embodiment of a pressurization assembly of this invention, shown in an opened state.

Referring now to FIG. 3A, a cross-sectional view of an embodiment of the PFD unit, generally 300, is shown, in its opened state, to include a housing 302 including a door 304 pivotally mounted to the housing 302 via a hinge 306. The housing 302 include a first connector 308 adapted to detachably and lockingly engage a second connector 310 on the door 304. The unit 300 also includes a bladder 312 disposed against an inner surface 314 of an interior 316 of the housing 302. The unit 300 is shown with a bio-compatible fluid container 318 disposed within the interior 316 of the housing 302 prior to closing.

Figure 3B:
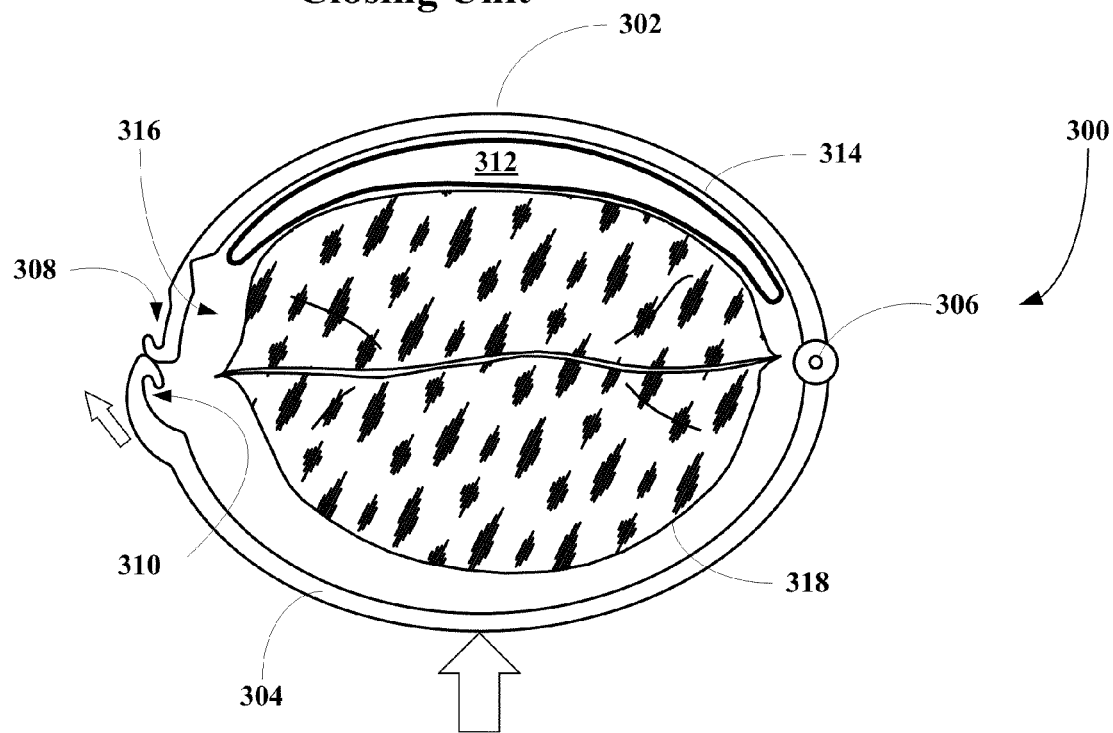
FIGS. 3B&C depict the pressurization assembly of FIG. 3A being closed.
Figure 3C:
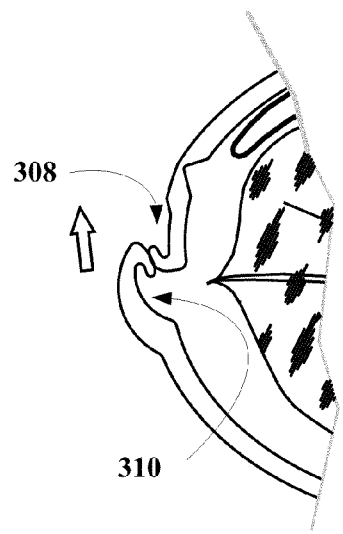
FIG. 3D depicts the pressurization assembly of FIG. 3A under pressure.
FIG. 3E depicts the pressurization assembly of FIG. 3A being opened after a fluid container is spent allowing removal and replacement of the fluid container.
FIGS. 3F&G depict an embodiment of a pressurization assembly of this invention having a pressure/rapid release valve in its closed state and opened state.

Referring now to FIGS. 3B&C, a cross-sectional view of the embodiment of the PFD unit 300 of FIG. 3A is shown being closed around the bio-compatible fluid container 318. The door connector 310 is pushed or snapped over the connector 308 to lock the unit 300 in its closed state.

Figure 3D:
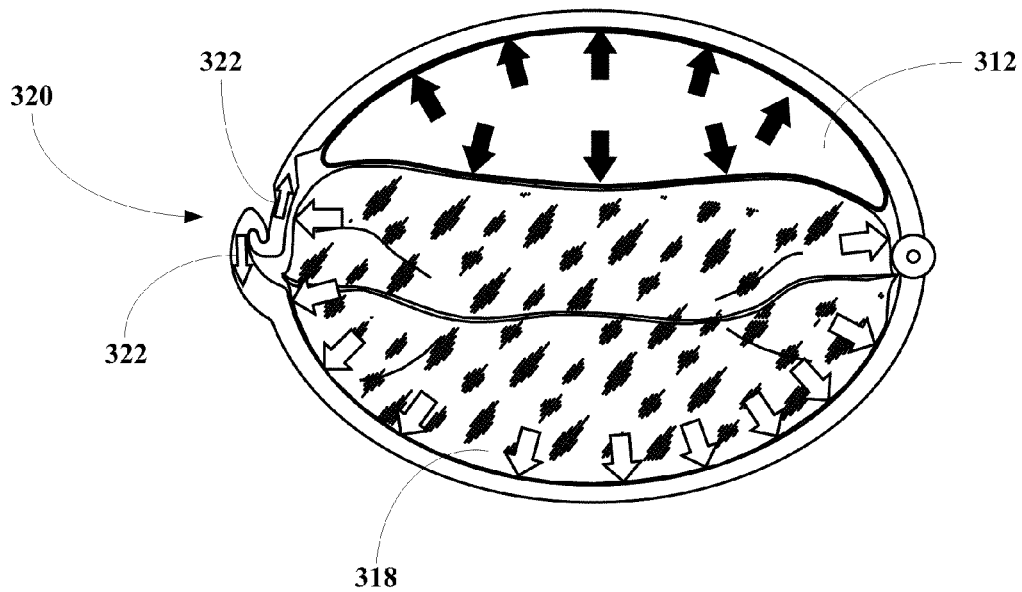
Figure 3E:
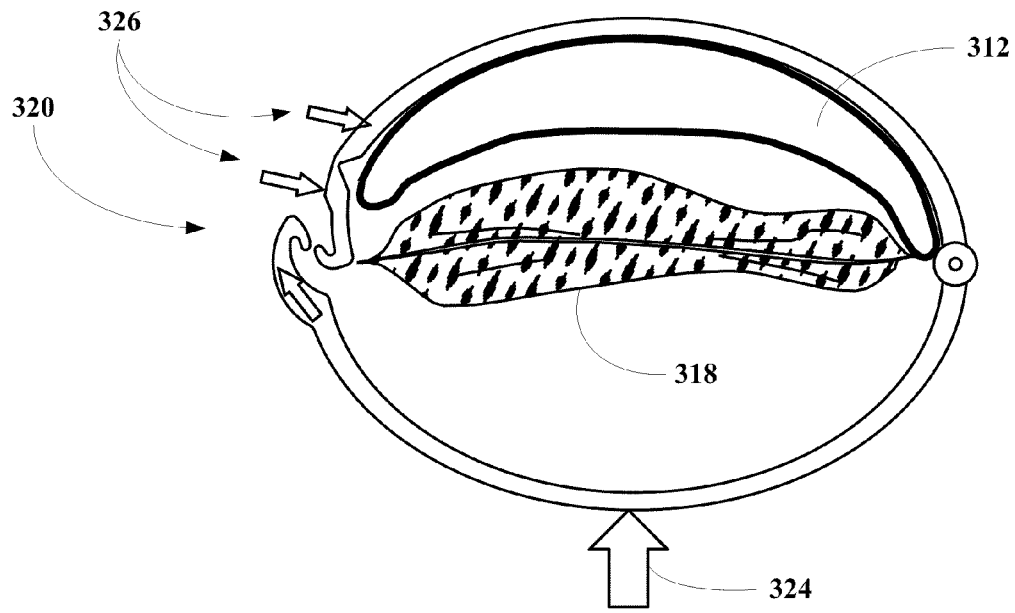

Referring now to FIGS. 3D&E, a cross-sectional view of the embodiment of the PFD unit 300 of FIG. 3D showing the inflation of the bladder 312, which results in an outward pressure indicated by the solid arrows. The outward pressure on the bladder 312 in turn imparts a pressure on the bio-compatible fluid container 318 as indicated by the open arrows. The door connector 310 is in its locked and closed state. The pressure from the bladder 312 onto the container 318 produced increases a locking force on the connection 320 as indicated by the arrows 322. Pressure in bladder 312, solid arrows, causes pressure against inside of door, open arrows, resulting in a tightening of the latch features between the housing and door. FIG. 3E illustrates how the connection 320 is disengaged after the container 318 has been exhausted (or is to be changed out) and the bladder 312 has been deflated (quickly as need requires). Arrows 324 and 326 illustrate the pressure points that are sufficient to cause the connection 320 to disengage. FIG. 3E shows that, after de-pressurizing bladder, door can easily be opened by pressure on the front of the case and the left area of the housing latch.

Figure 3F:
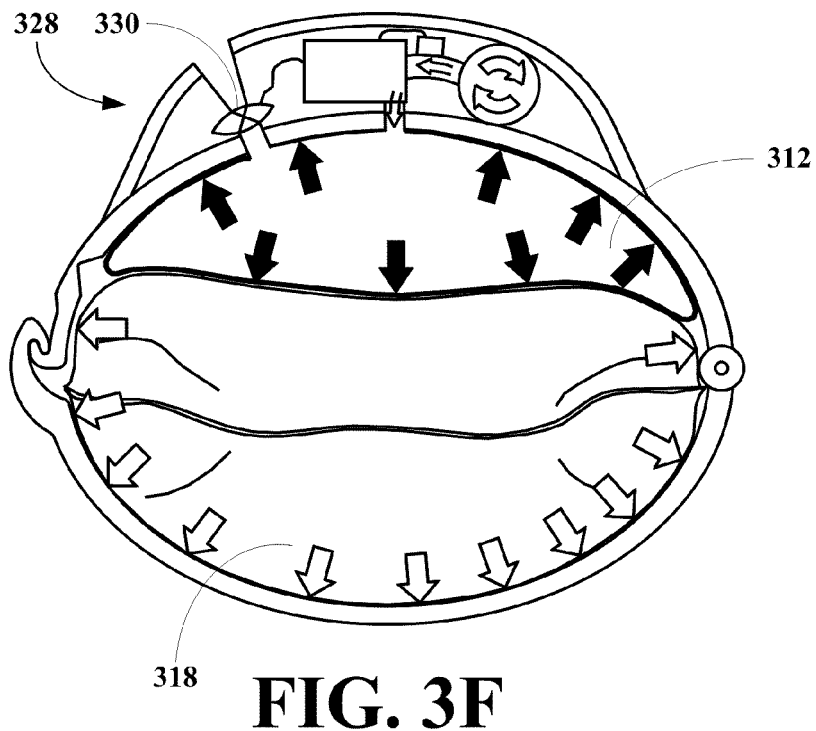
Figure 3G:
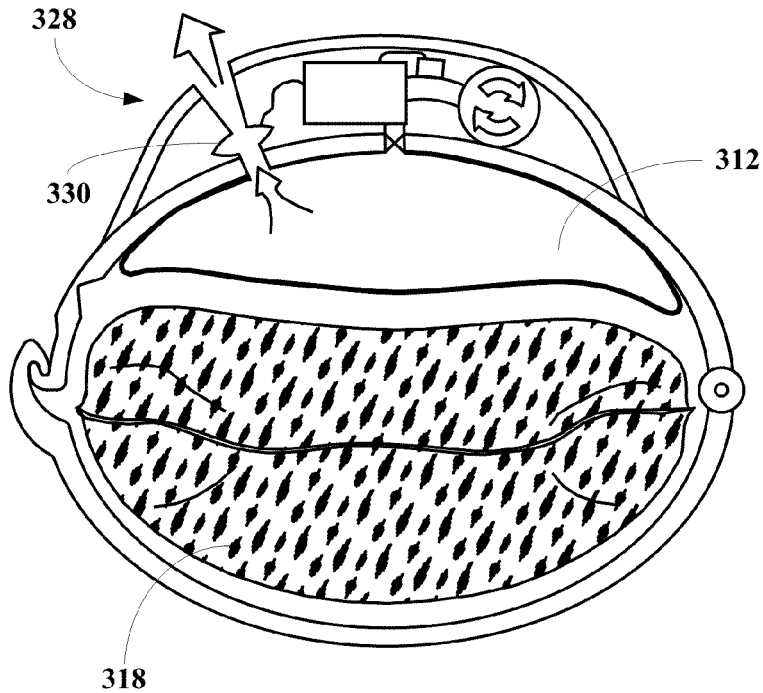

Referring now to FIGS. 3F&G, a cross-sectional view of the embodiment of the PFD unit 300 of FIG. 3F illustrates a fast pressure release system 328 of this invention in its closed state. FIG. 3F shows the bladder 312 and bag 318 under pressure and the rapid exhaust valve 330 (at about 11 o'clock on the back of the housing) closed. FIG. 3G illustrates the system 328 in its opened state to quickly reduce the pressure in the bladder 312. FIG. 3G shows the rapid exhaust valve 332 open. This condition serves 2 purposes—first it is an emergency stop which instantly reduces the bag to gravity flow. Second it takes the pressure off the latch, facilitating quick removal of the old bag. Any remaining gas such as air in the bladder is quickly evacuated by the placement of a new bag in the case and closing the door.

Figure 4A:
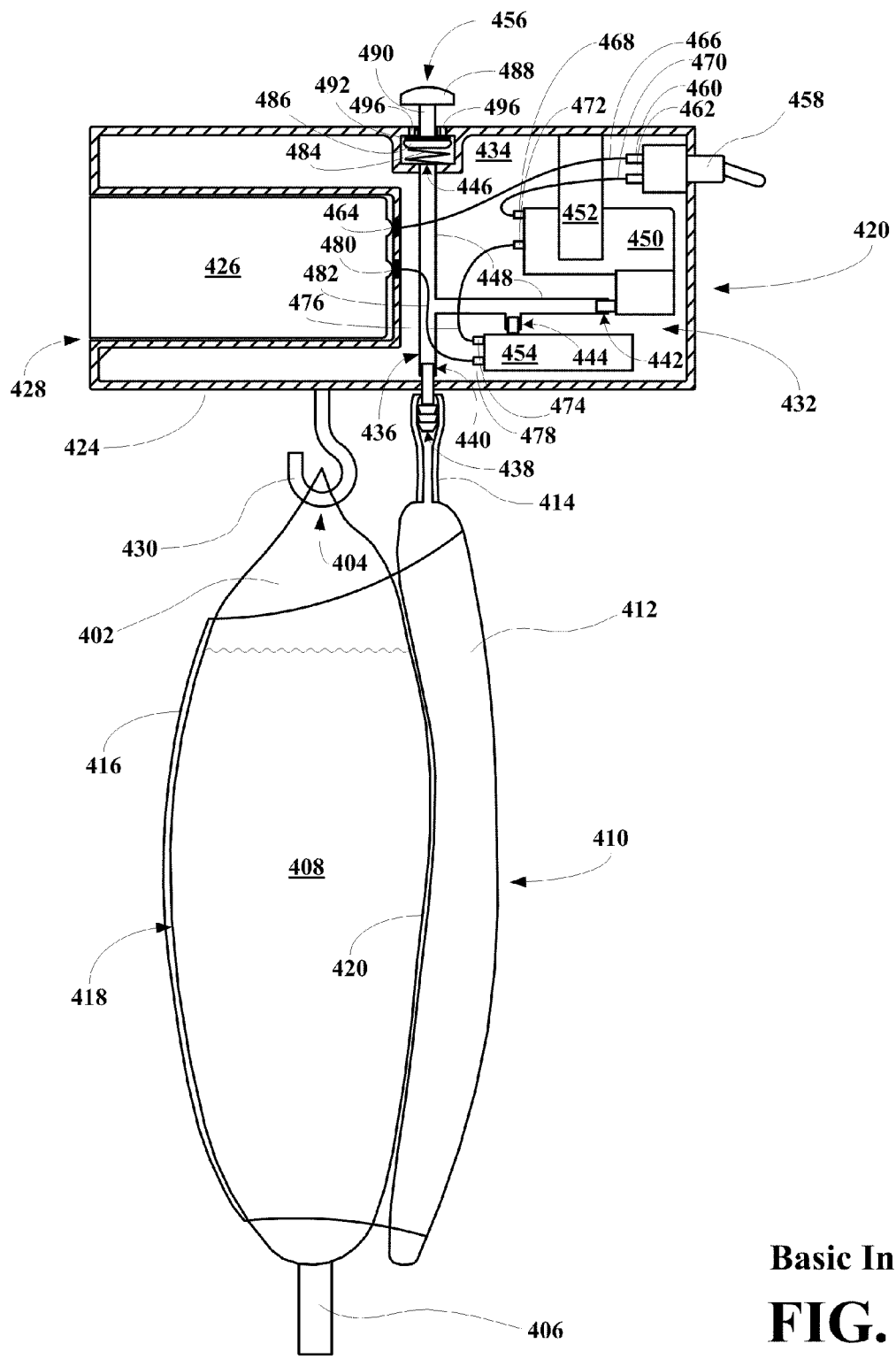
FIG. 4A depicts an embodiment of a basic infuser apparatus of this invention.

Referring now to FIG. 4A, a cross-sectional view of an embodiment of the basic infuser apparatus, generally 400, is shown to include an IV bag 402 having a top aperture 404 and a tube 406 for transmitting a fluid 408 in the bag to a patient. The apparatus 400 also includes a bladder assembly 410 having a bladder 412 having an inflation/deflation tube 414 and a pressure sleeve 416. The sleeve 416 surrounds a portion 418 of the bag 402 with the bladder 412 adjacent one side 420 of the bag 402 so that as the bladder 412 is inflated, pressure is distributed on the portion 418 of the bag from the bladder 412 and the sleeve 416. The apparatus 400 also includes a pressurization assembly 422. The assembly 422 includes a housing 424. The housing 424 includes a battery pack 426 inserted into a battery receptacle 428. The housing 424 also includes a hook 430 for supporting the bag 402 and the bladder assembly 410. The housing 424 also includes a bladder pressure control assembly 432 situated in a bladder pressure control assembly cavity 434. The control assembly 434 includes a tubing network 436. The network 436 includes a tubing fitting 438, where the fitting 438 receives the bladder inflation/deflation tube 414. The network 434 also includes four ends 440, 442, 444 and 446, with tubing interconnecting 448 the ends 440, 442, 444, and 446. The first end 440 is connected to the fitting 438. The second end 442 is connected to a pump 450 mounted by a mount 452 in the cavity 434 of the housing 424. The third end 444 is connected to a pressure sensor and control switch 454. And, the fourth end 446 is connected to a pressure release assembly 456. The assembly 432 also includes an ON/OFF switch 458. The ON/OFF switch 458 includes a two switch leads 460 and 462. The first switch lead 460 is connected to a first battery terminal 464 of the battery pack 426 by a first wire 466. The second switch lead 462 is connected to a first pump lead 468 of the pump 450 via a second wire 470. A second pump lead 472 is connected to a first sensor lead 474 via a third wire 476. A second sensor lead 478 is connected to a second battery terminal 480 of the battery pack 426 via a fourth wire 482. The pressure release assembly 456 includes a spring 484, a plunger 486 connected to a release button 488 via a shaft 490. The assembly 456 also includes a seal 492 disposed on a top 494 of the plunger 486. The assembly 456 also includes vents 496 so that when the button 488 is depressed, gas such as air in the bladder 412 is vented to the surroundings through the vents 496. Of course, it should be recognized that any other pressure release biased assembly can be used to release the bladder pressure either in a controlled or emergency manner—uncontrolled rapid release as is well known in the art and include solenoid valves, pilot operated valves, flapper valves, duckbill valves, or any other valve operable herein.

Figure 4B:
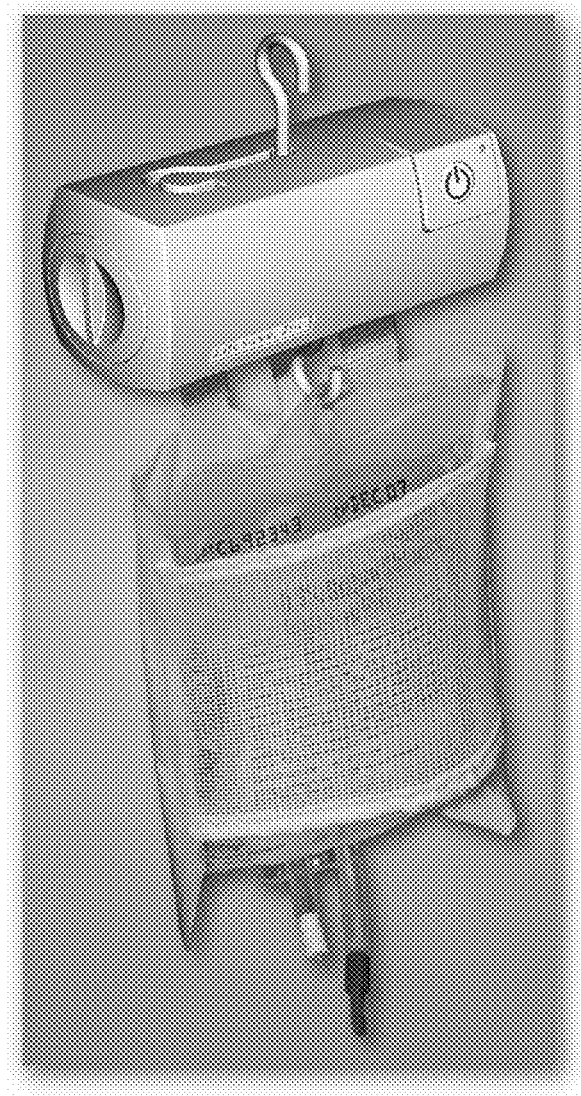
FIGS. 4B-D depict 3D renderings of a particular commercial embodiment of the basic infuser apparatus of FIG. 4A.
Figure 4C:
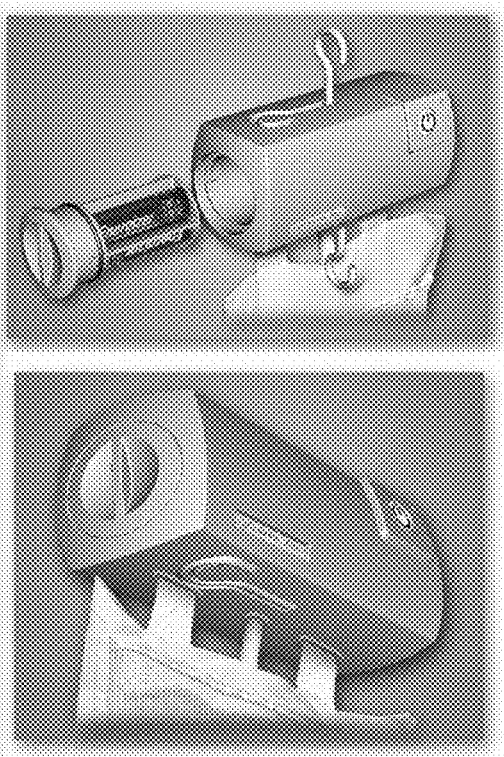
Figure 4D:

Referring now to FIGS. 4B-D, three 3D renderings of a particular commercial embodiment of the apparatus of FIG. 4A described above is illustrated, where the bladder assembly is actually suspended from the pressurization assembly via adjustable straps instead of a hook as shown in FIG. 4A.

Figure 5:
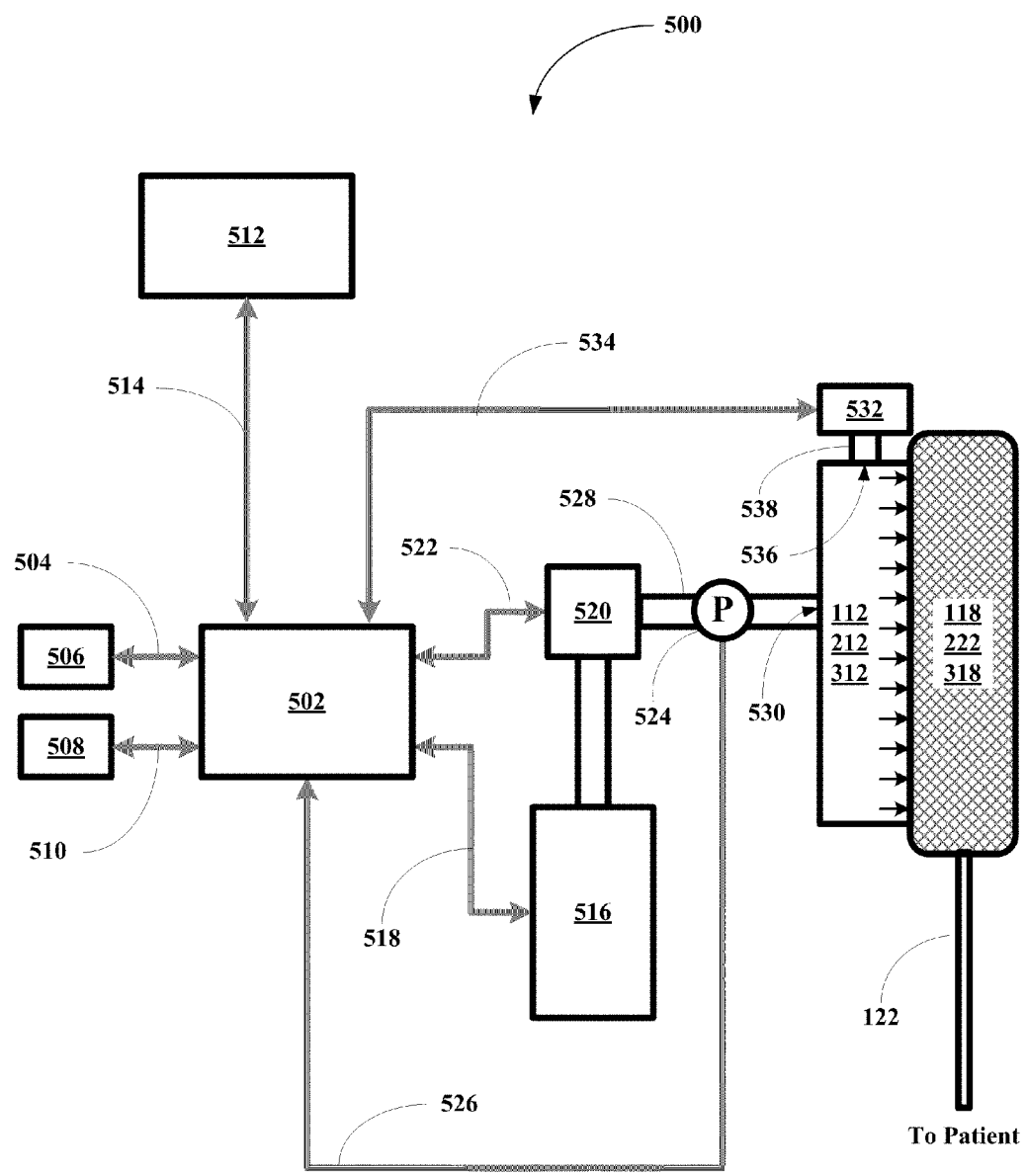
FIG. 5 depicts an embodiment of an apparatus of this invention including a pressurization assembly.

Referring now to FIG. 5, a control diagram of an embodiment of an apparatus of FIG. 1A, generally 500, is shown in a control unit 502, which is generally a processing unit (analog or digital processing unit or micro processing unit). The control or processing unit 502 controls the functioning of all other apparatus components, which in turn controls a pressure in the bladder and thereby a pressure on the BCF container to control fluid flow out of the container. The processing unit 502 includes communication hardware and software so that it can send and receive information via a communication link 504, which can be connect to a remote monitor unit 506. The communication link 504 can be a bi-directional wired link or a bi-directional wireless link depending on the exact design and where the apparatus 500 is being used. The apparatus 500 can also include a manual interface 508 adapted to permit manual control of the processing unit 502 either via a set of buttons or via a programming interface through a manual control link 510. The apparatus 500 can also include an output device 512 such as display device or other device for monitoring the performance of the apparatus 500 during use. The output device 512 is connected to the processing unit 502 via an output data link 514. The apparatus 500 also includes a pump 516. The pump 516 is connected and controlled by the processing unit 502 via a bi-directional pump control link 518. The apparatus 500 also includes a control valve 520. The control valve 520 is connected and controlled by the processing unit 502 via a bi-directional control valve link 522. The apparatus 500 also includes a pressure sensing unit 524. The pressure sensing unit or pressure sensor 524 is connected to the processing unit 502 via a pressure data link 526. The sensor 524 measures a pressure in a gas (e.g., air, nitrogen, or the like) supply conduit 528 connecting the valve 520 to the inflation/deflation opening 530 in the bladder 112, 212 or 312. The pump 516 and the valve 520 in conjunction control the gas pressure in the bladder 112, 212 or 312. As the bladder 112, 212 or 312 is inflated, the bladder 112, 212 or 312 will exert a force (indicated by the arrow pointing toward a BCF container 118, 222 or 318), which controls the fluid flow rate out of the conduit 122 to the patient. The apparatus 500 also includes a rapid release valve 532. The rapid pressure release valve 532 is connected and controlled by the processing unit 502 via a bi-directional pressure release valve control link 534. The pressures release valve 532 is connected to a pressure release port 536 via a pressure release conduit 538, but it may be integral with the bladder 112, 212 or 312.

Figure 6A:
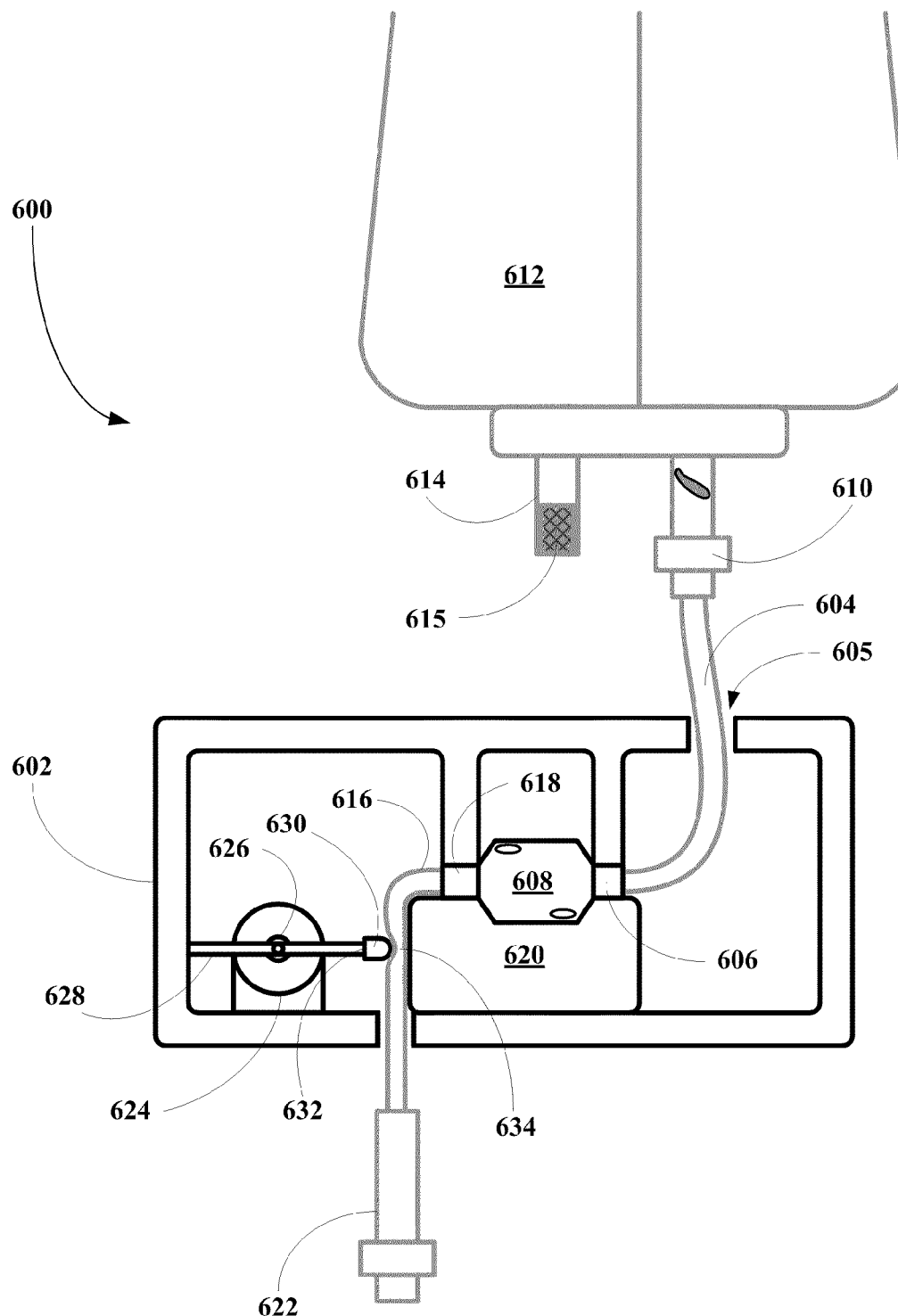
FIG. 6A depicts an embodiment of an apparatus of this invention including a flow control unit.
Figure 6B:
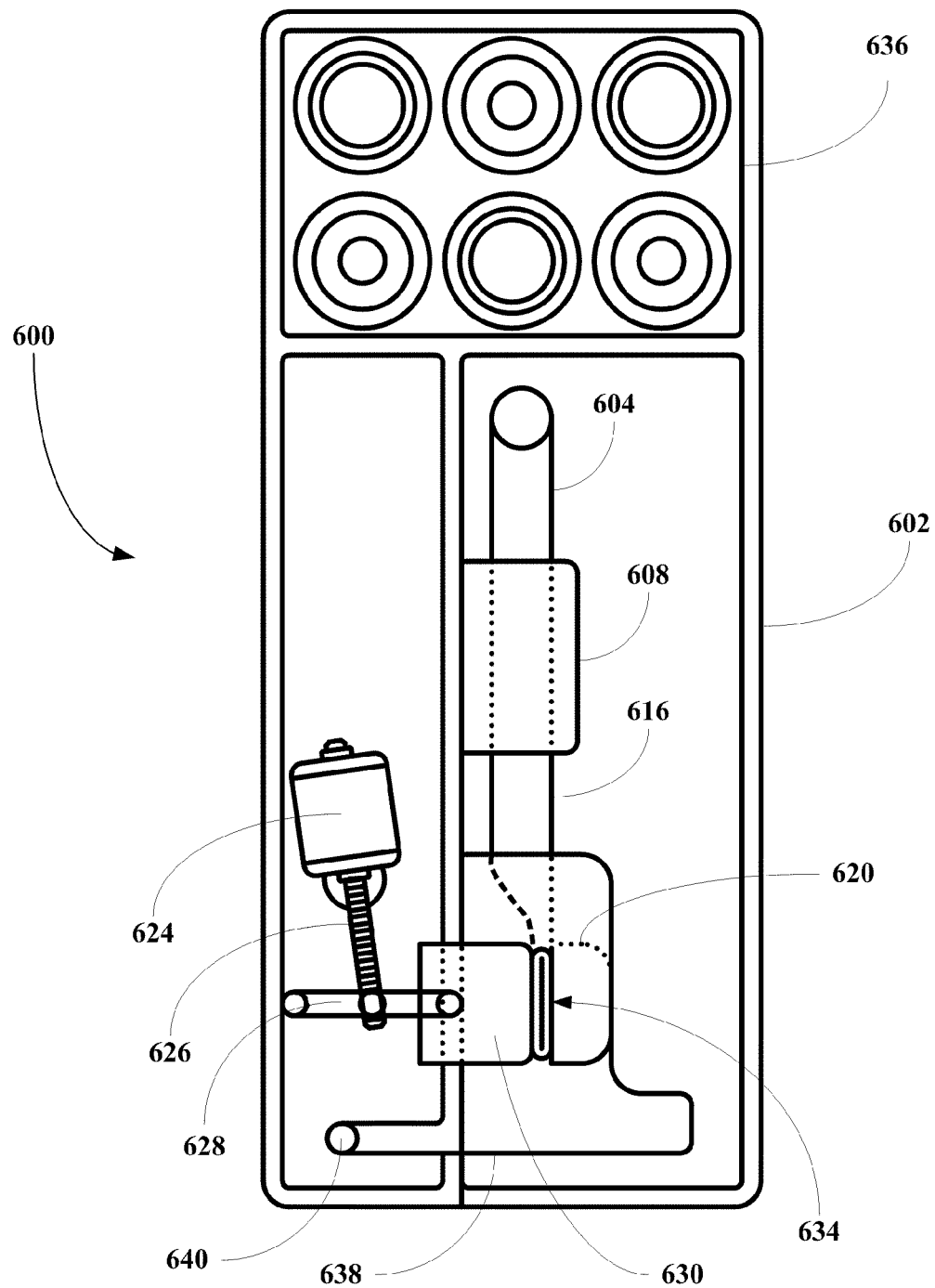
FIGS. 6B&C depict an embodiment of another apparatus of this invention including a flow control unit, in closed state and opened state, respectively.

Referring now to FIG. 6A, an embodiment of a fluid flow control (FFC) unit of this invention, generally 600, is shown to include a housing 602 and a tubing section 604 connected between an inlet port 606 of an air bubble sensor 608 of the FFC unit 600 and a fitting 610 of a BCF container 612 and passing through an aperture 605 in the housing 602. The BCF container 612 is shown here to include a med port 614 having a septum 615. A second tubing section 616 is connected to an outlet port 618 of the air bubble sensor 608 passing through the FFC unit 600 adjacent a clamping block 620 and connecting to an external fitting 622. The FFC unit 600 also include a motor 624 having a shaft 626 operating a toggle 628. The toggle 628 includes a clamp 630 at its distal end 632. The motor 624 moves the toggle 628 so that the clamp 630 pushes the tubing section 616 at a clamping position 634 against the clamping block 620 restricting fluid flow through the second tubing section 616. The FFC unit 600 also include a battery pack 636 as shown in FIGS. 6B&C. By varying the clamping force exerted by the clamp 630 against the tubing section 616 at the clamping position 634, the fluid flow control unit 600 controls a flow rate of the fluid delivered to the patient.

Referring now to FIG. 6B, a cross-sectional view of the fluid flow control (FFC) unit 600 of FIG. 6A is shown with the toggle 628 situated so that the clamp 630 fully clamps the tubing section 616 at the clamping position 634 shutting off all flow through the tubing section 616. The FFC unit 600 also includes a retaining block 638 pivotally mounted in the housing 602 on a pivot 640. In FIG. 6B, the retaining block 638 is shown in its closed configuration.

Figure 6C:
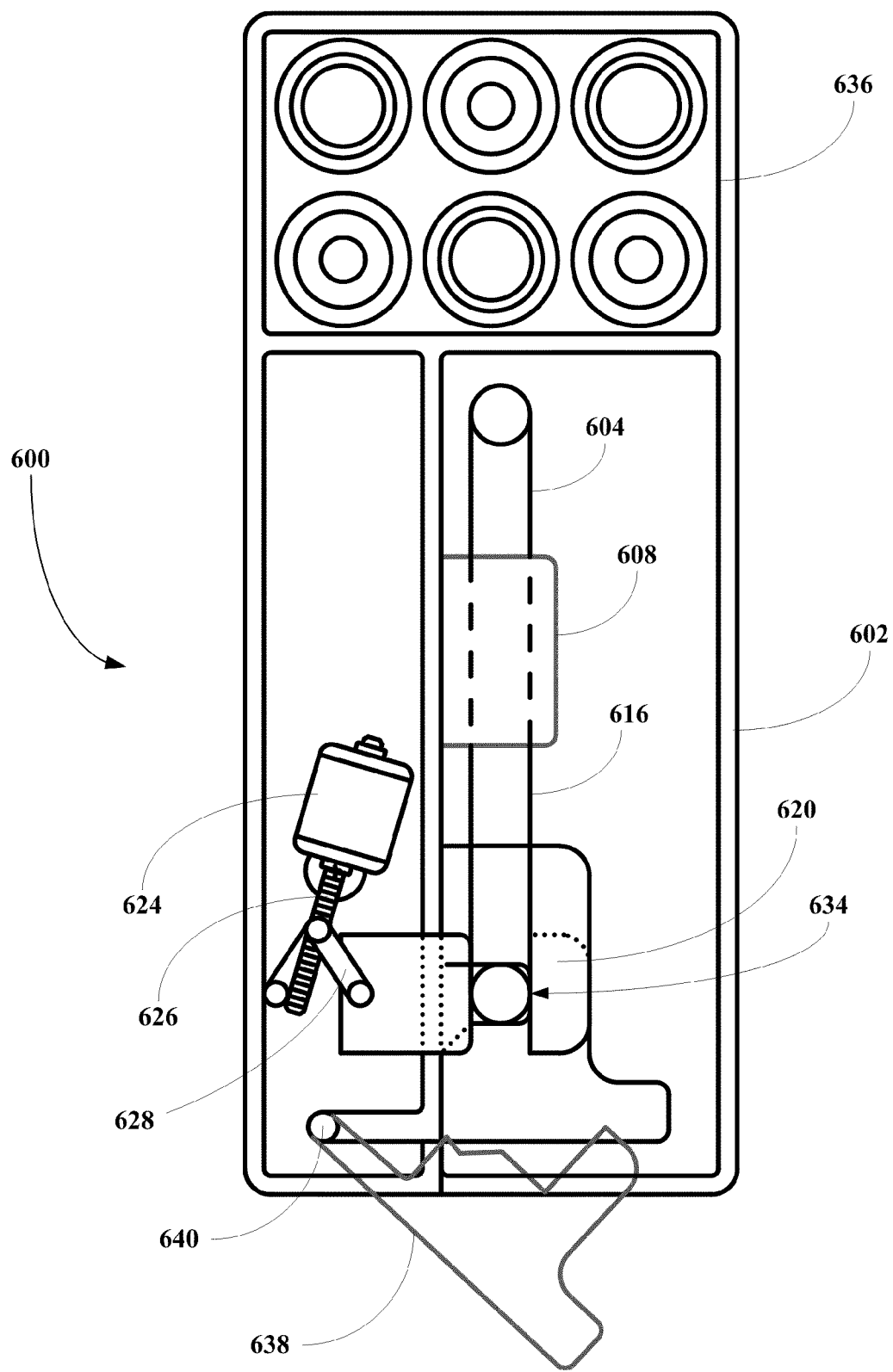

Referring now to FIG. 6C, a cross-sectional view of the fluid flow control (FFC) unit 600 of FIG. 6A is shown with the toggle 628 situated so that the clamp 630 fully opens the tubing section 616 at the clamping position 634 allowing full fluid flow through the tubing section 616. In FIG. 6C, the retaining block 638 is shown in its opened configuration. It should be recognized that by changing the position of the toggle 628 and thereby the clamp 630, the fluid flow through the tubing section 616 can be varied and controlled. Alternatively, by transitioning back and forth between a clamped state and an opened state with a specific duty cycle, the mean flow rate of fluid through the tubing section 616 can be controlled.

Figure 7A:
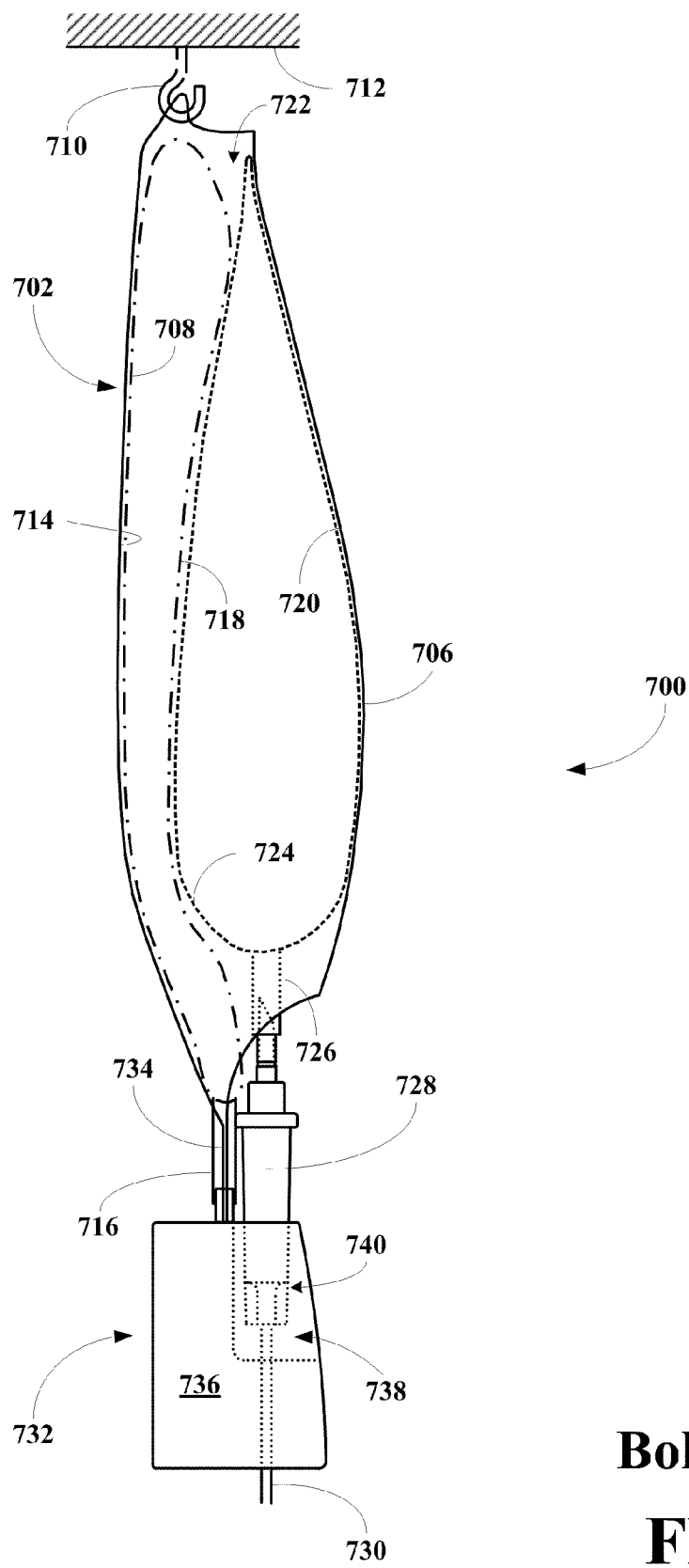
FIGS. 7A&B depict a side view and a front view of an embodiment of an embodiment of a bolus infuser of this invention.
Figure 7B:
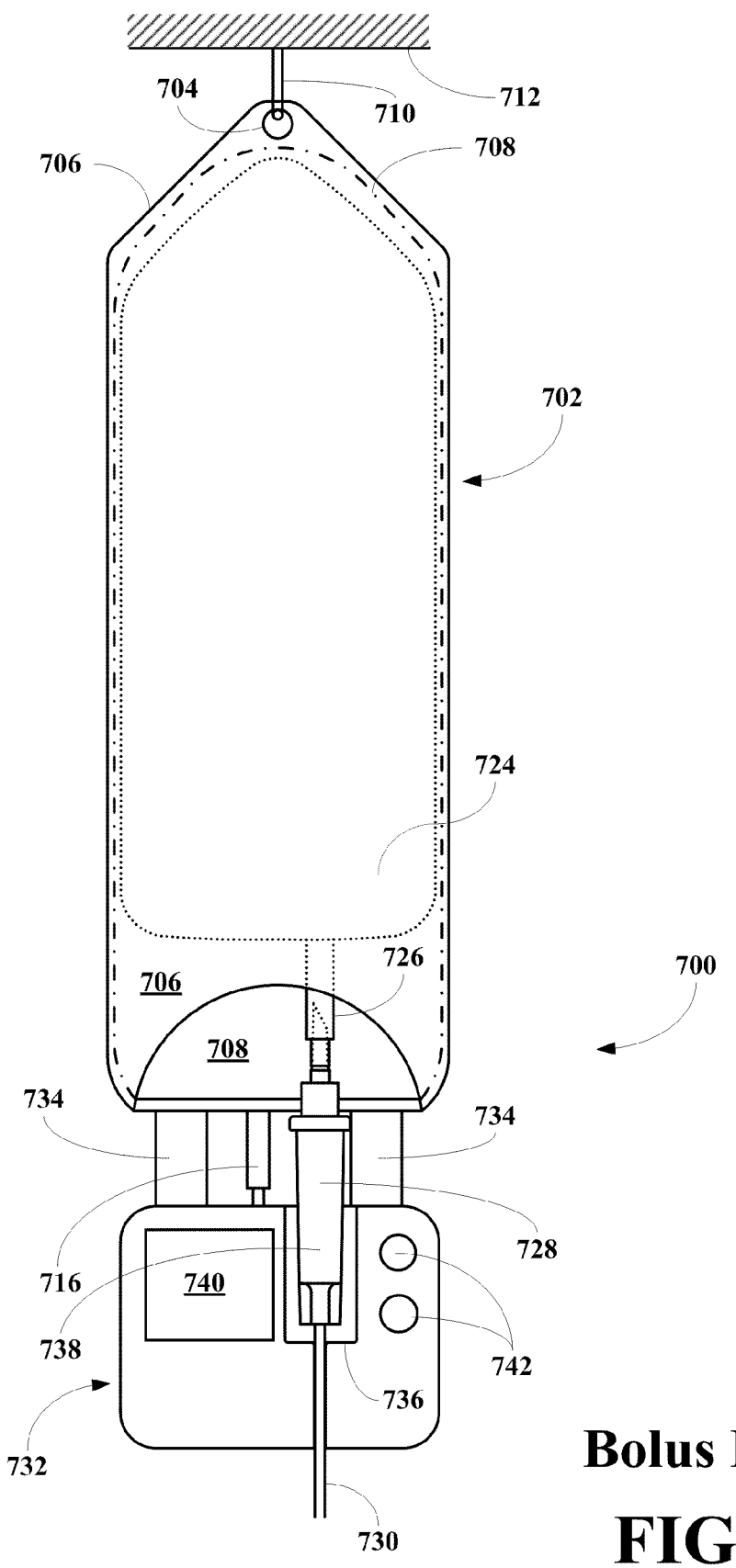
FIG. 7C depicts an expanded view of the flow control assembly of the bolus infuser of FIGS. 7A&B.
FIGS. 7D-F depict 3D renderings of a particular commercial embodiment of the bolus infuser apparatus of FIGS. 7A-C.

Referring now to FIGS. 7A&B, a side view and front view of an embodiment of a bolus infuser, generally 700, is shown to include a bladder assembly 702. The bladder assembly 702 includes a top aperture 704 for hanging the assembly 702, a sleeve 706 and a bladder 708. The apparatus 700 is shown here hanging from a hook 710 anchored to or associated with a support structure 712. The bladder 708 is situated adjacent an interior rear surface 714 of the sleeve 706. The bladder 708 includes an inflation/deflation tube 716. A front surface 718 of the bladder 708 and an interior front surface 720 of the sleeve 706 forms an IV bag pocket 722 for receiving an IV bag 724 so that the sleeve 706 surrounds the IV bag 724. The IV bag 724 includes an output tube 726, a drip chamber 728 and a flow tube 730 adapted to supply a fluid from the IV bag to a patient. The apparatus 700 also includes a housing 732. The housing 732 is attached to the sleeve 706 by a plurality of adjustable straps 734 (here the plurality of two) for adjusting a position of the housing 732 relative to the bladder assembly 702. The housing 732 includes a cavity 736 for receiving a lower portion 738 of the drip chamber 728. The housing 732 also includes a display 740 and switches 742.

Figure 7C:
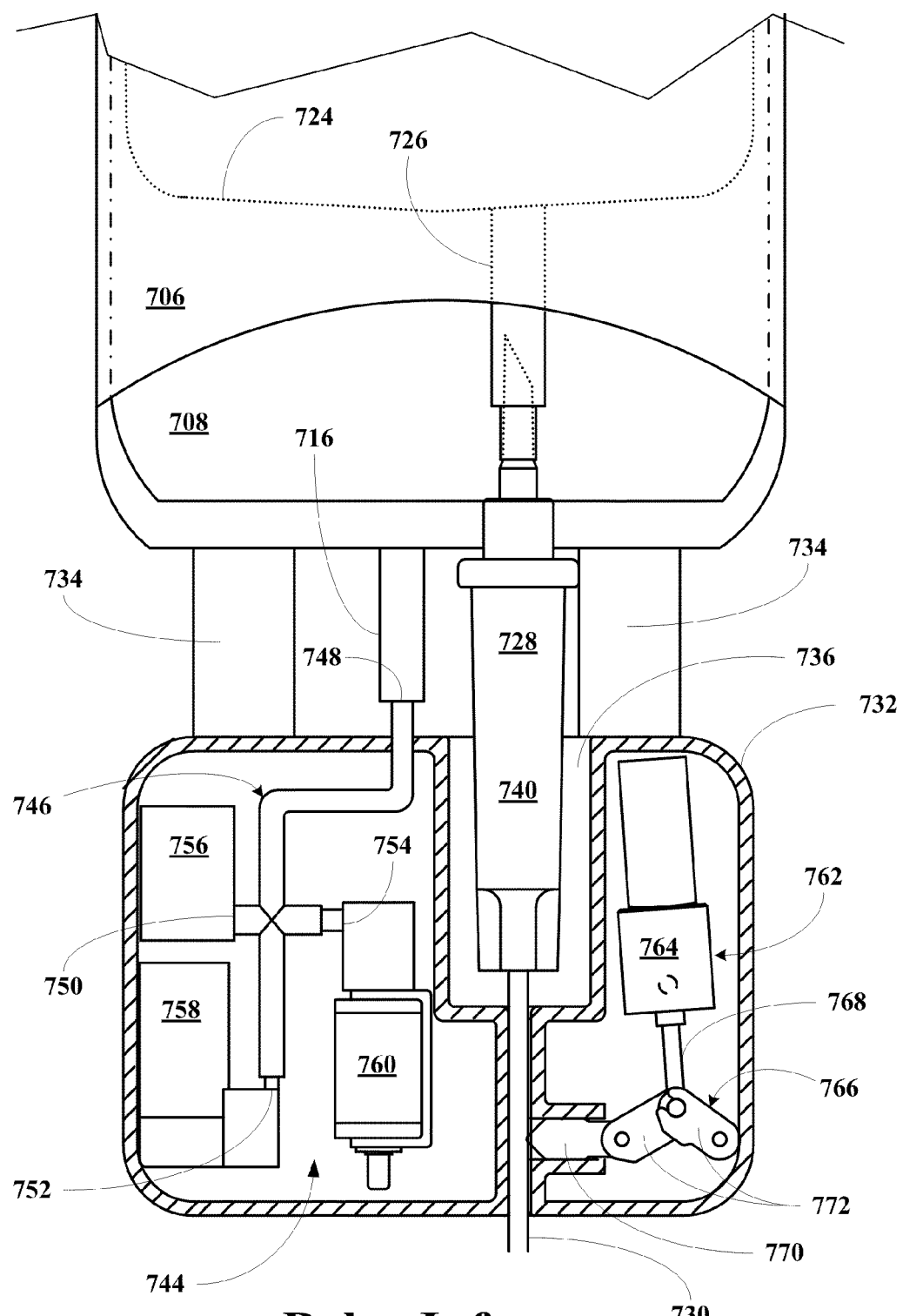

Referring now to FIG. 7C, a cross-sectional view of the housing 732 is shown, where the housing 732 is shown to further include a bladder pressurization assembly 744. The bladder pressurization assembly 744 includes a tubing network 746 including four ends 748, 750, 752 and 754. The first end 748 is connected to the bladder inflation/deflation tube 716. The second end 750 is connected to a pressure sensor and control switch 756. The third end 752 is connected to a pump 758. And, the fourth end 754 is connected to a solenoid release valve 760.

The housing 732 also mounts a flow control assembly 762. The flow control assembly 762 includes a motor 764 connected to a toggle means 766 via a shaft 768. The toggle means 766 is connected to a pinch block 770. The toggle means 766 includes two members 772 pivotally mounted on a distal end 774 of the shaft 768. As the shaft 768 is pushed down by the motor 764, the members 772 of the toggle means 766 straight propelling the pinch block 770 against the flow tube 730 restricting the flow through the flow tube 730 to the patient. The pressure sensor and control switch 756 controls the pump 758 for inflating the bladder 708, while the solenoid release valve 760 control deflation of the bladder 708. By a careful control of the inflation pressure and duration via the switch 756 and the pump 758 and a careful control of the flow control assembly 762, a controlled bolus of fluid may be administered to the patient. Of course, it should be recognized that any other means for occluding the flow through a flow tube can be used as well, such means are well known in the art and include linear actuators, solenoids and other similar devices. Of course, the apparatus 700 also includes a power supply which can be a battery pack as described in other embodiments of infusers herein or the apparatus 700 can be plugged into an external AC or DC power supply.

Figure 7D:
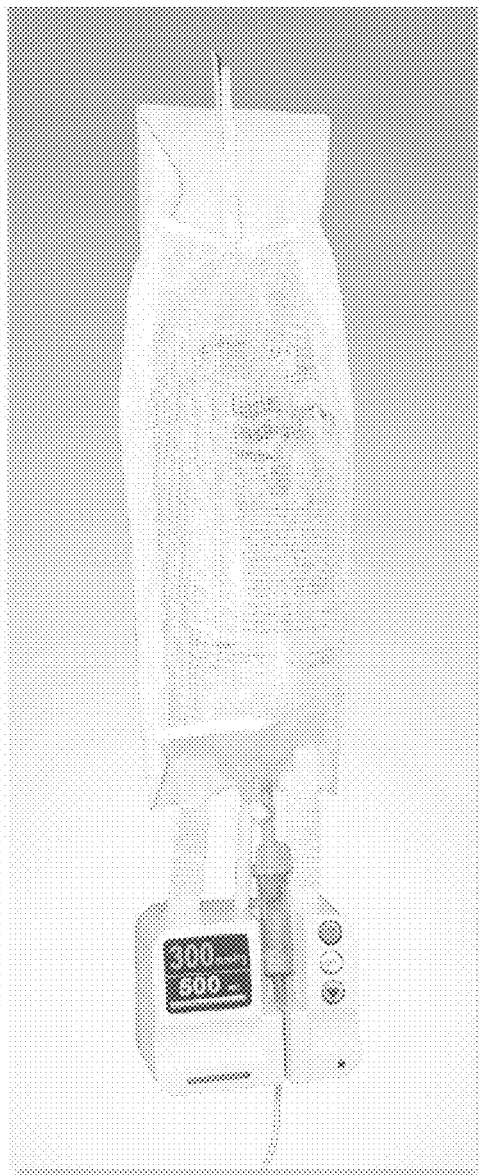
Figure 7E:
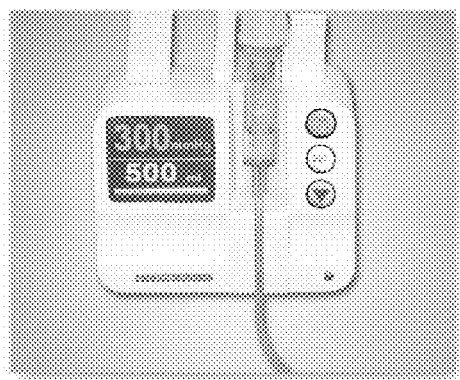
Figure 7F:

Referring now to FIGS. 7D-F, three 3D renderings of a particular commercial embodiment of the apparatus of FIG. 7A described above is illustrated.

Figure 8:
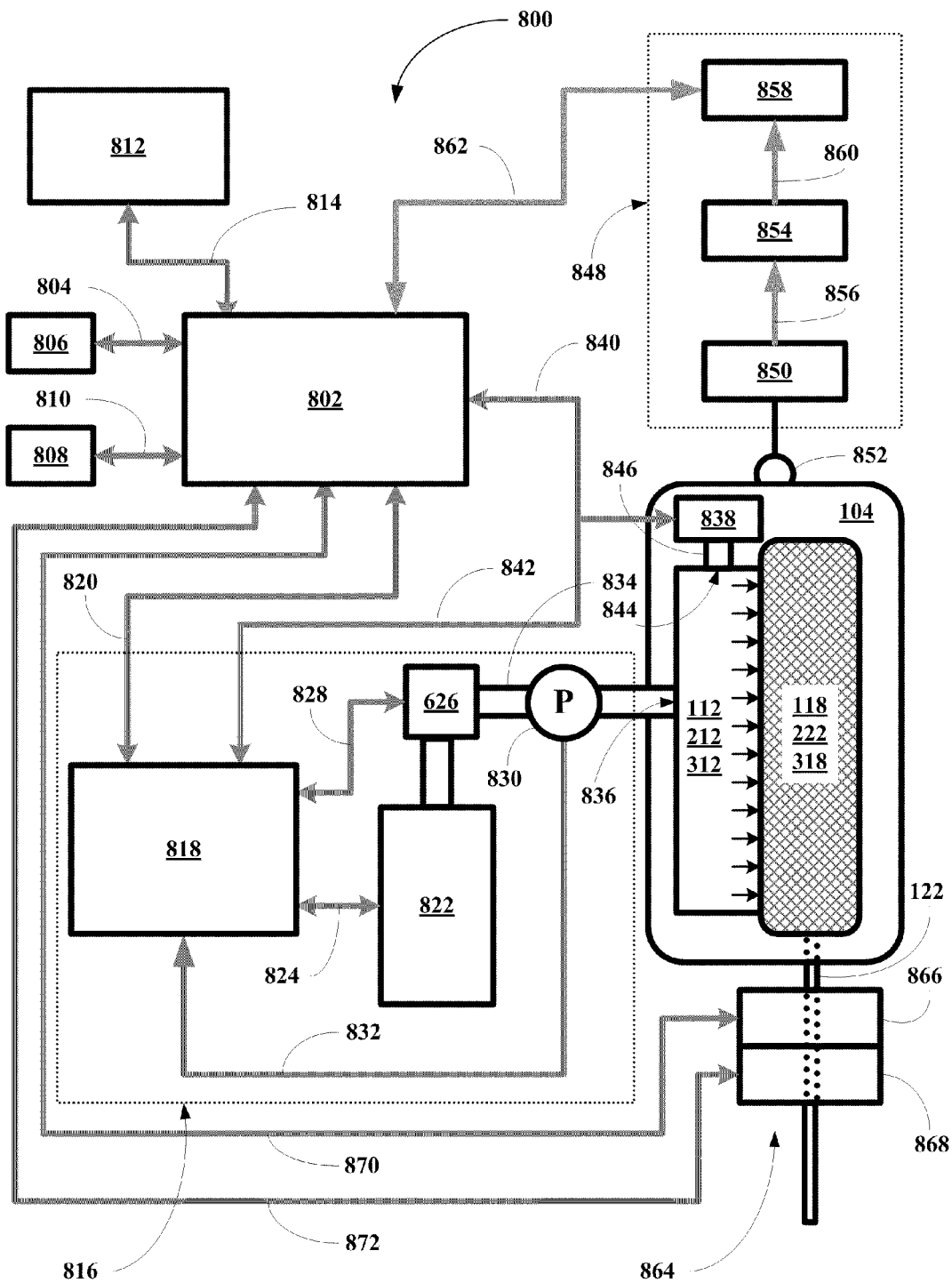
FIG. 8 depicts an embodiment of an apparatus of this invention including a pressurization assembly, a weight monitoring assembly and a flow control assembly.

Referring now to FIG. 8, a control diagram of an embodiment of an apparatus 100 of FIG. 1D, generally 800, is shown to include a central control unit 802, which is generally a processing unit (analog or digital processing unit or micro processing unit). The central control unit 802 controls the functioning of all other apparatus components, which in turn controls a pressure in the bladder and the flow rate through the FFC unit. The central control unit 802 includes communication hardware and software so that it can send and receive information via a communication link 804, which can be connect to a remote monitor/control unit 806. The communication link 804 can be a uni-directional or bi-directional wired link or wireless link depending on the exact design and where the apparatus 800 is being used. The apparatus 800 can also include a manual interface 808 adapted to permit manual control of the central control unit 802 either via a set of buttons or via a programming interface through a manual control link 810. The apparatus 800 can also include an output device 812 such as display device or other device for monitoring the performance of the apparatus 800 during or subsequent to use. The output device 812 and/or record-keeping device is connected to the processing unit 802 via an output data link 814. The apparatus 800 also includes a pressurization unit 816. The pressurization unit 816 includes a pressurization control unit 818 connected to the central control unit 802 via a bi-directional control and data link 820. The pressurization unit 816 includes a pump 822 connected and controlled by the pressurization control unit 818 via a bi-directional pump control link 824. The pressurization unit 816 also includes a control valve 826. The control valve 826 is also connected and controlled by the pressurization control unit 818 via a bi-directional pump control link 828. The pressurization unit 816 also includes a pressure sensing unit 830. The pressure sensing unit or pressure sensor 830 is connected to the pressurization control unit 818 via a pressure data link 832. The sensor 830 measures a pressure in an air supply conduit 834 connecting the valve 826 to the inflation/deflation opening 836 in the bladder 112, 212 or 312. The pump 822 and the valve 826 in conjunction control the air pressure in the bladder 112, 212 or 312. As the bladder 112, 212 or 312 is inflated, the bladder 112, 212 or 312 will exert a force (indicated by the arrow pointing toward a BCF container 118, 222 or 318), which controls the fluid flow rate out of the conduit 122 to the FFC unit. The apparatus 800 also includes a rapid release valve 838. The rapid pressure release valve 838 is connected and controlled by either the central control unit 802 or the pressurization control unit 818 via a bi-directional pressure release valve control links 840 and 842, respectively. The pressures release valve 838 is connected to a pressure release port 844 via a pressure release conduit 846, but it may be integral with the bladder 112, 212 or 312. The apparatus 800 also includes a weight measuring and monitoring (WMM) unit 848. The WMM unit 848 includes a load cell 850. The load cell 850 supports the bladder housing 104 via a connection 852. The load cell 850 is adapted to determine the weight of the housing 104, which includes the bladder 112, 212 or 312 and the BCF container 118, 222 or 318. The load cell 850 is connected to an amplifier 854, which is adapted to amplify an output signal received from the load cell 850, via a load cell signal link 856. The WMM unit 848 also includes a vibration filter 858, which receives an output from the amplifier 854 via an amplifier signal link 860. The vibration filter 858 is adapted to correct the amplifier output to remove vibration noise from the signal. The vibration filter 858 generates an output that is forwarded to the central control unit 802 via a vibration filter link 862. The apparatus 800 also includes a fluid flow control (FFC) unit 864. The FFC unit 864 includes an air bubble sensor 866 and a flow restrictor 868. The bubble sensor 866 is connected to the central control unit 802 via a bubble sensor data link 870, while the flow restrictor 868 is connected to the central control unit 802 via a flow restrictor data link 872. One embodiment of a flow restrictor 868 is shown in FIGS. 5A-C and described in the associated text. However, any flow restrictor or regulator can be used provided that it can be controlled by the central control unit. Thus, the apparatus 800 can control a pressure in the bladder, monitor an amount of fluid left in the BCF container, and control a flow rate of fluid to a patient. The control units can comprise any type of control device including an analog or digital processing unit, micro controllers, or any other type of electronic device that can monitor data and regulate or control power or data streams to controllable components.

Figure 9A:
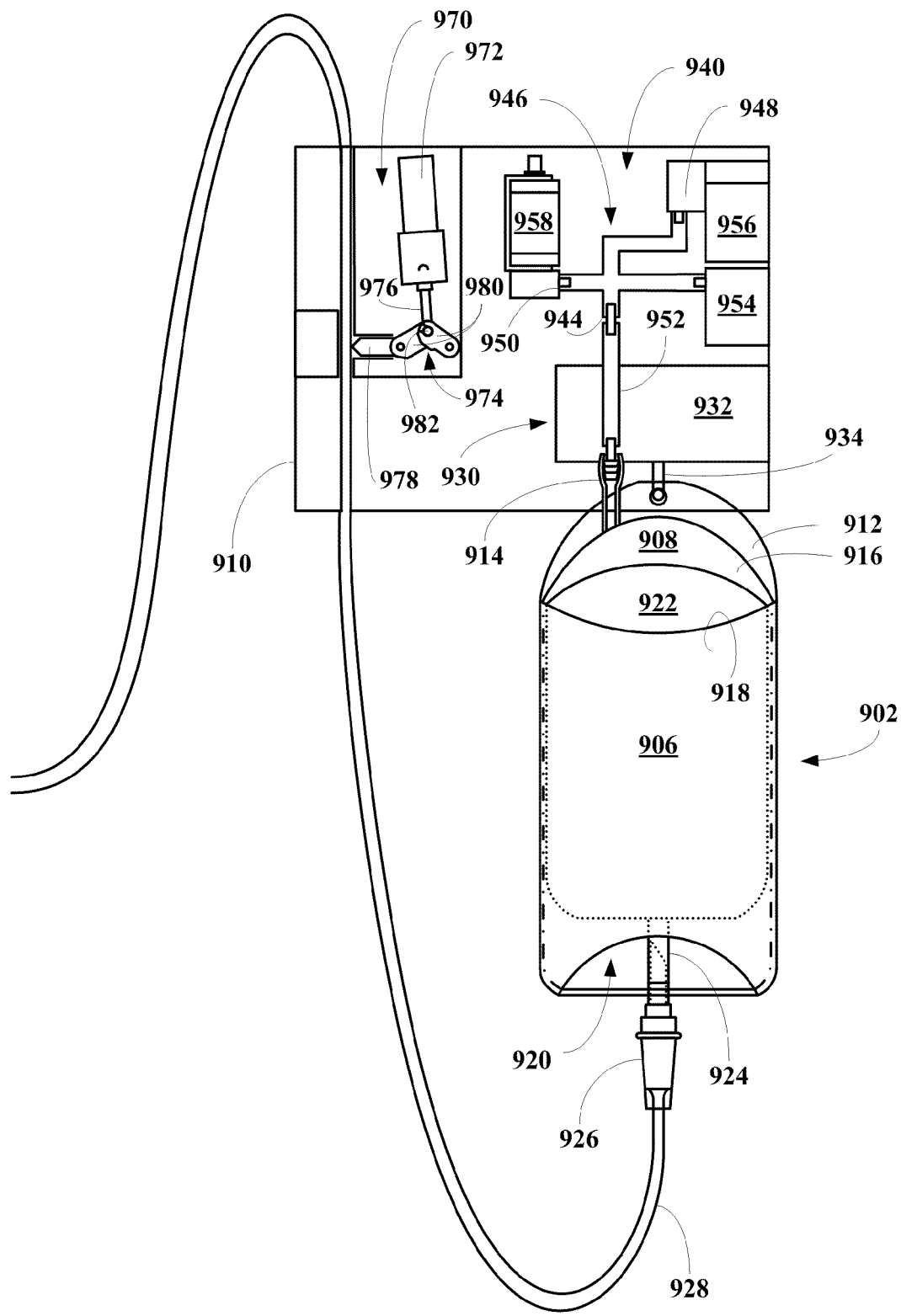
FIG. 9A depicts a top configured embodiment of an apparatus of this invention including a pressurization assembly, a weight monitoring assembly and a flow control assembly.

Referring now to FIG. 9A, an apparatus of this invention, generally 900, is shown to include a bladder assembly 902. The bladder assembly 902 includes a top aperture 904 for hanging the assembly 902, a sleeve 906 and a bladder 908. The apparatus 900 also includes a housing 910. Within the housing 910, the apparatus 900 includes a load cell assembly 930, a bladder pressurization assembly 940, a flow control assembly 970.

The bladder assembly 902 is configured with the bladder 908 situated adjacent an interior rear surface 912 of the sleeve 906. The bladder 908 includes a inflation/deflation tube 914. A front surface 916 of the bladder 908 and an interior front surface 918 of the sleeve 906 forms an IV bag pocket 920 for receiving an IV bag 922 so that the sleeve 906 surrounds the IV bag 922. The IV bag 922 includes an output tube 924, a drip chamber 926 and, a flow tube 928 adapted to supply a fluid from the IV bag to a patient.

The load cell assembly 930 include a load cell 932 having a hanger 934, where the hanger 934 is adapted to receive the aperture 904 of the bladder assembly 902 so that the load cell 932 can measure a weight of the bladder assembly 902. The load cell 932 may measure the weight of the bladder assembly 902 on a continuous, semi-continuous, periodic, intermittent or mixed basis (mixed meaning a combination of continuous, semi-continuous, periodic, or intermittent measuring protocol).

The bladder pressurization assembly 940 includes a tubing network 942 including four ends 944, 946, 948 and 950 and a spacer tube 952. The first end 944 is connected to the spacer tube 952, which is in turn connected to the bladder inflation/deflation tube 914. The second end 946 is connected to a pressure sensor and control switch 954. The third end 948 is connected to a pump 956. And, the fourth end 950 is connected to a solenoid release valve 958. The spacer tube 952 is adapted to ensure that the bladder assembly 902 hangs freely from the load cell apparatus 930. The bladder pressurization assembly 940 also includes a fitting 960 for receiving the bladder inflation/deflation tube 914. The pressure sensor and control switch 954 controls the pump 956 for inflating the bladder 908, while the solenoid release valve 958 controls deflation of the bladder 908. By a careful control of the inflation pressure and duration via the switch 954 and the pump 956 and a careful control of the flow control assembly 970, a controlled bolus of fluid or a precise rate of flow may be administered to the patient. Of course, it should be recognized that any other means for occluding the flow through a flow tube can be used as well, such means are well known in the art and include linear actuators, solenoids and other similar devices.

The flow control assembly 970 includes a motor 972 connected to a toggle means 974 via a shaft 976. The toggle means 974 is connected to a pinch block 978. The toggle means 974 includes two members 980 pivotally mounted on a distal end 982 of the shaft 976. As the shaft 976 is pushed down by the motor 972, the members 980 of the toggle means 974 straight propelling the pinch block 978 against the flow tube 928 restricting the flow through the flow tube 928 to the patient. Of course, the apparatus 900 also includes a power supply which can be a battery pack as described in other embodiments of infusers herein or the apparatus 900 can be plugged into an external AC or DC power supply.

Referring now to FIGS. 9B-D, three 3D renderings of a particular commercial embodiment of the apparatus of FIG. 9A described above are illustrated including a display and controls.

The apparatus 900 is arranged with the housing including the pump, power supply and controls for a pressure infuser equipped a load cell (transducer or strain gage type weighing scale), where the housing is situated above the bladder assembly. The sleeve, bladder and bag would hang directly from the connection of the load cell so that the sleeve, bladder and bag may be weighed on any basis including continuous. The housing may either be hung from an IV pole, clamped to a pole or attached by any other solid support. The load cell is capable of detecting changes in the weight of the bag which can be directly converted to an amount of fluid dispensed to the patient. The apparatus 900 uses a standard tubing set with drip counter plugged into the IV bag. The tubing is then looped from below the drip counter and inserted into a groove or slot in the housing disposed above the bladder assembly. The tube would enter the housing through the slot, pass through a shut-off mechanism of the flow control assembly, out of the case and to the patient.

An embodiment of the apparatus 900 could also be laid on its side or in any position. The dispensing of the fluid would be controlled by the pump and shut-off mechanism. The load cell weighing function would not be functional during the time the device is not vertical, but would resume its measurements when the case was raised so that the sleeve and bag hung freely below the housing. The housing and IV bag need not be placed above the patient to function properly, since the dispensing of IV fluid is controlled by the pressure in the sleeve due to inflation of the bladder and the shut-off mechanism.

The apparatus 900 also have the advantage that the shut-off mechanism and load cell both are contained in a single housing, eliminating the need to have a load cell above the bladder assembly and a shut-off mechanism or flow control assembly disposed below the bladder assembly. This arrangement simplifies the product and reduces size and cost as well as easing the control by placing all components in the same case.

Another advantage of the apparatus 900 is that pulling on the tubing set does not extent any force on the bladder assembly, and therefore does not interfere with the readings of fluid dispensed based on the change in weight detected by the load cell.

NEW MATERIAL

Flow Rate Calculations

Several alternate embodiments for measuring the flow rate out of an IV fluid bag, whether pressurized or gravity flow, are presented.

Method for Estimating Flow from a Pressure-Flow-Drag Relationship

It is well known that laminar fluid flow Q in a rigid cylindrical tube with radius r and length L can be described by Poiseuille's equation:

$$Q = \frac{\Delta P \pi r^4}{8\mu L}$$

where $\Delta P$ is the pressure drop across the cylinder and $\mu$ is dynamic viscosity of the fluid.

However, empirical data of flow in an IV tube showed a non-linear relationship, perhaps due to turbulent flow, entrance effects, elasticity of the IV tubing, and other unknown factors which defy theoretical analysis.

Figure 10A:
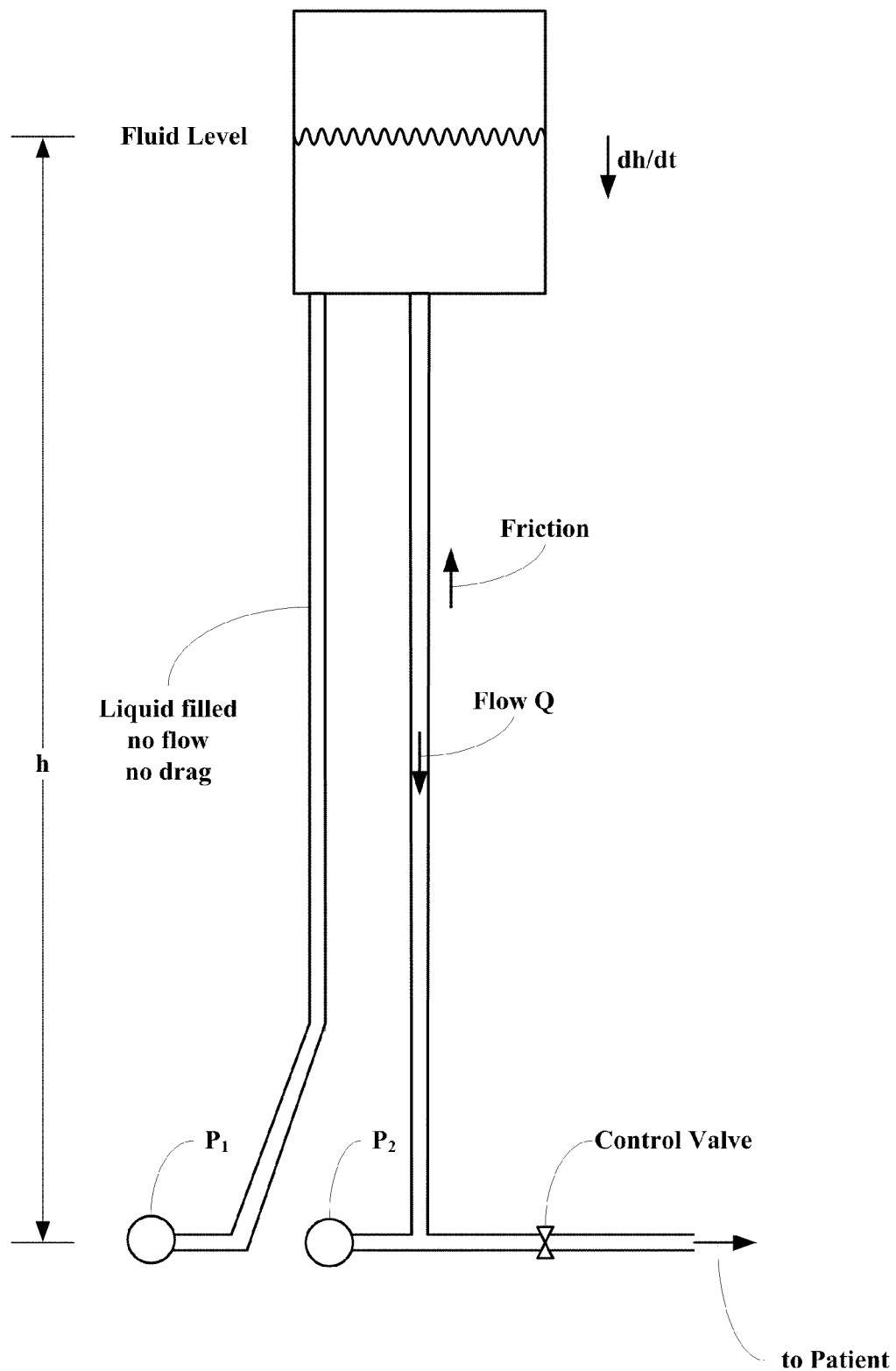
FIGS. 10A&B depict an embodiment of an apparatus of this invention including a pressurization assembly and a flow metering and control assembly.

We determined the non-linear relationship using the systems shown in FIGS. 10A&B and developed the necessary equation for estimation of flow in a particular commercial infusion set using experimental data from pressure transducers and flow meters collected during experiments from IV infusions into anesthetized swine.

We also present a mechanism for using continuous pressure measurements at a single site to calculate flow. The pressure measurement site is between the IV fluid bag and the IV catheter with pressure measured before and during flow. In this embodiment the flow clamp must be placed downstream from the $P_2$ pressure measurement site, see FIGS. 10A&B. The analysis is substantially simplified and permits a direct expression if a second transducer is used to find the driving pressure $P_1$ of FIG. 10A or gas bag pressure $P_A$ of FIG. 10B.

Further background is provided by the following derivation. In the absence of flow, $P_2$ is equal to the driving pressure $P_1$, which is determined by the gas pressure $P_A$ and hydrostatic pressure $\rho g h$ of the column of fluid trapped in the tubing:

$$P_2|_{flow=0} = P_1 + P_A + \rho g h$$

During infusion, $P_2$ is reduced by the frictional forces which impede flow.

$$P_2 = P_2|_{flow=0} - P_{friction}$$

$$P_{friction} = P_A + \rho g h - P_2 = P_1 - P_2$$

We empirically relate the frictional pressure drop to flow and tubing wall pressure and solve for the flow Q:

$$Q = f(P_1, P_2)$$

In the first arrangement, depicted in FIG. 10A, infusion is controlled by the action of gravity on the fluid and a height differential h between the infusion reservoir and the infusion site. Under these conditions $P_A = 0$ and $P_1 = \rho g h$. Several embodiments are possible, including, but not limited to, a purely passive flow meter which measures the pressures $P_1$ and $P_2$ and computes the flow Q, to a bolus controller which automatically and fully opens and closes the control valve when the desired bolus volume has been delivered, to a negative-feedback flow controller which partially opens the control valve to obtain a desired flow.

As a refinement, the pressure sensor $P_1$ may be eliminated for a slight increase in uncertainty. To compute $P_1$, only h(t) must be determined. Furthermore, $dh/dt = -Q/A$ and the cross-sectional area A is a characteristic of the IV bag, which may be assumed to be known within reasonable accuracy. Therefore we may measure the initial h at $P_2$ before infusion begins $$P_2|_{t+} = \rho g h|_{t=0}$$

Through the application of numeric integration to recursively estimate Q(t) and h(t), a single pressure sensor measuring $P_2$ before and during infusion suffices to estimate flow within clinical precision.

Figure 10B:
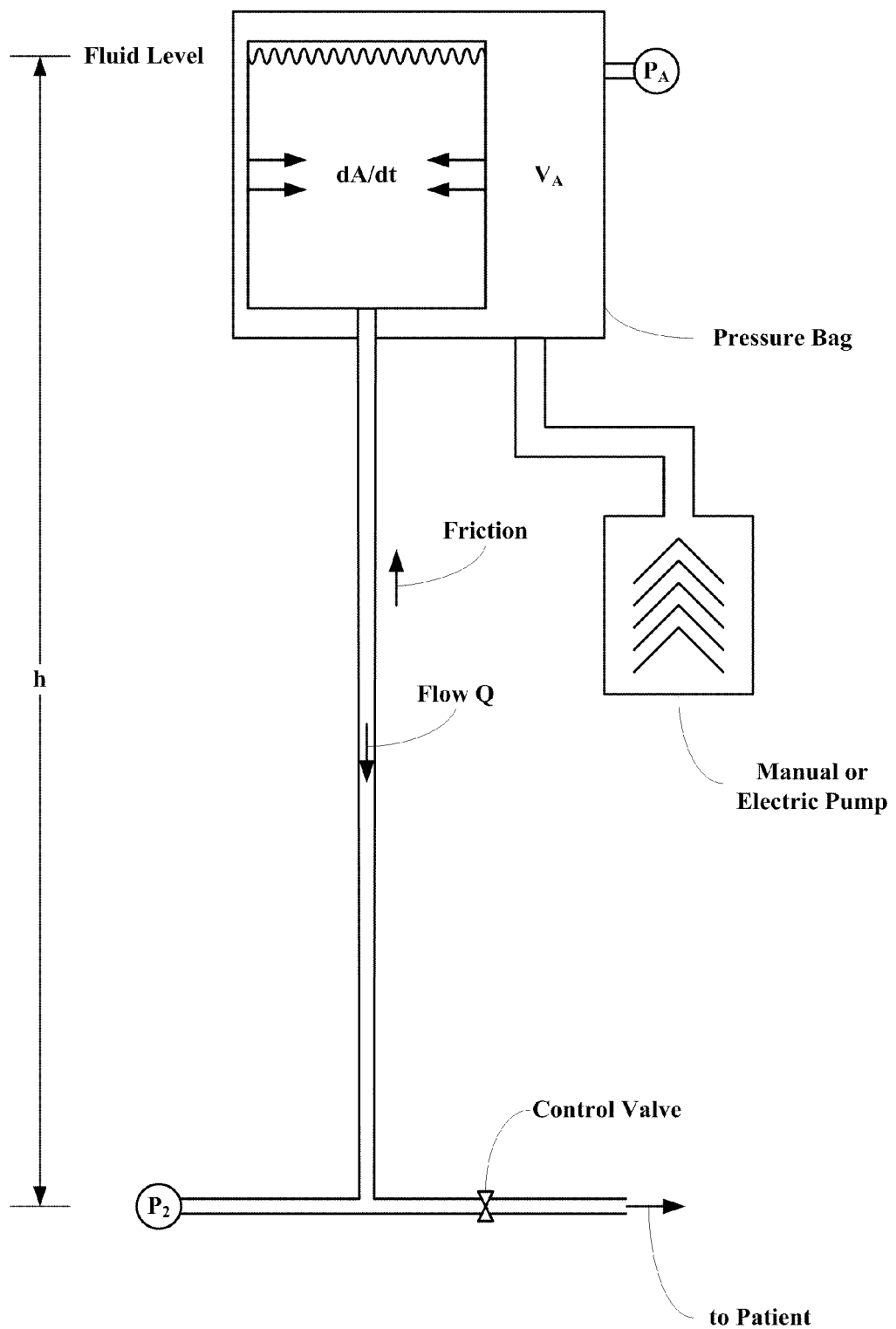

In the second arrangement, depicted as FIG. 10B, a pressure bag is inflated to exert horizontal force on the reservoir and to increase the fluid delivery rate. In this case, the IV bag collapses without the fluid level significantly dropping, so h is maintained constant during the infusion. Again several embodiments are possible, including, but not limited to, a purely passive flow meter, a bolus controller with manual inflation of the pressure bag, a bolus infuser with automatic inflation of the pressure bag, a flow controller which adjusts the control value to obtain desired flow, and a feedback-based pressure infuser, which adjusts the inflation pressure $P_A$ of the pressure bladder to obtain desired flow.

From inspection of empirical data we chose the following general form for the pressure-flow relationship:

$$Q = \frac{c_1 P_A^2 + c_2 P_A P_2 + c_3 P_2^2 + c_4 P_A + c_5 P_2 + c_6}{c_7 P_A^2 + c_8 P_A P_2 + c_9 P_2^2 + c_{10} P_A + c_{11} P_2 + c_{12}}$$

The following coefficients were empirically determined for a Baxter 2C6401s infusion set used with an adaptation of the pressure bag embodiment of the present invention:

| | |
|---|---|
| $c_1$ | 367 |
| $c_2$ | −884 |
| $c_3$ | 681 |
| $c_4$ | −1.71e+003 |
| $c_5$ | 294 |
| $c_6$ | 2.75e+004 |
| $c_7$ | 7.39 |
| $c_8$ | −20.1 |
| $c_9$ | 14.1 |
| $c_{10}$ | 81.3 |
| $c_{11}$ | −19.9 |
| $c_{12}$ | 1.49e+003 |

Figure 11:
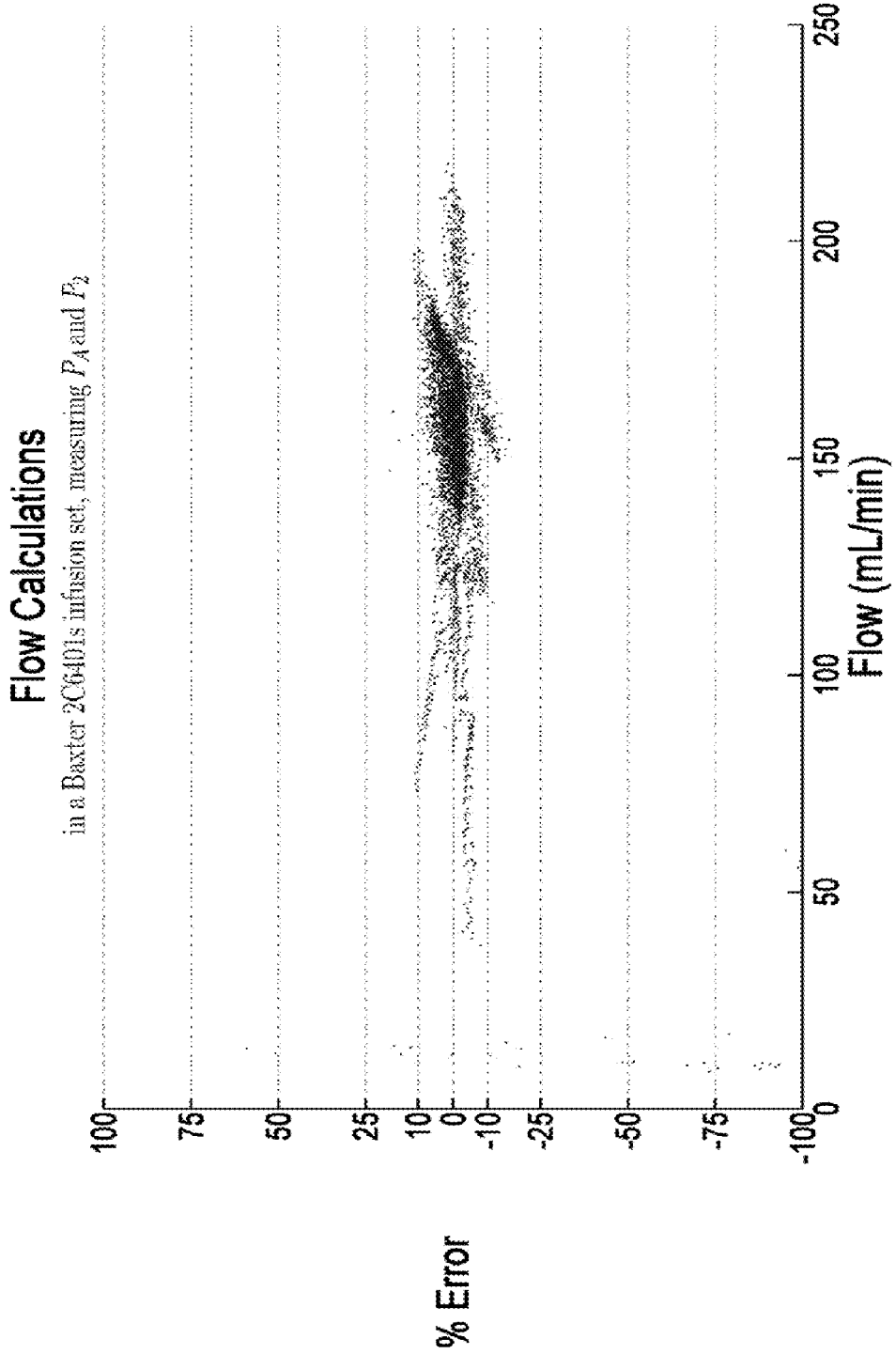
FIG. 11 depicts a scatter plot of percent error estimate vs. flow rate in mL/min in laboratory testing of the flow metering devices of FIGS. 10A&B.

Referring now to FIG. 11, experimental data is plotted from 4 swine studies showing the percentage error in estimated flow, which is generally within 10% compared to an ultrasonic transit time flow probe.

As a refinement, we find that it is again possible to eliminate the pressure sensor $P_A$ and calculate $P_1$. Using a pressure bladder at room temperature, h remains constant during infusion while $P_A$ varies. Yet, $P_A V_A$ is constant according to Boyle's Law, where $V_A$ is the steadily expanding volume of the pressure bladder. Also, the pressure bladder expands into the volume vacated by the IV fluid according to the rate of flow.

Boyle's Law provides as follows:

$$P_A(t)V_A(t) = \text{constant}$$

$$P_A(t)V_A(t) = (P_A|_{t=0^-})(V_A|_{t=0^-})$$

$$P_A(t) = \frac{(P_A|_{t=0^-})(V_A|_{t=0^-})}{V_A(t)}$$

We can now define volumetric flow as follows:

$$Q(t) = \frac{d}{dt}V_A(t)$$

$$\int_{\tau=0}^{t} Q(\tau)d\tau = \int_{\tau=0}^{t} \frac{d}{d\tau}V_A(\tau)d\tau$$

$$\int_{\tau=0}^{t} Q(\tau)d\tau = \int_{\tau=0}^{t} dV_A(\tau)$$

$$\int_{\tau=0}^{t} Q(\tau)d\tau = V_A(t) - (V_A|_{t=0^-})$$

$$\int_{\tau=0}^{t} Q(\tau)d\tau + (V_A|_{t=0^-}) = V_A(t)$$

This results in a final expression for $P_A$:

$$P_A(t) = \frac{(V_A|_{t=0^-})}{(V_A|_{t=0^-}) + \int_{\tau=0}^{t} Q(\tau)d\tau}(P_A|_{t=0^-})$$

An initial measure of $P_A$ derived from $P_2|_{flow=0}$ suffices to estimate flow during the bolus by recursive estimation of Q(t) and $P_A(t)$.

Method for Estimating Flow by Mass Exchange with an Inelastic Calibration Chamber An embodiment of a flow estimation device is described for use with the infusers of this invention, which obtains an accurate estimate of an effluent fluid flow rate and/or estimate of fluid volume remaining. This method neither requires suspension in a gravitational field nor sterile pressure transducers, and therefore, may be used regardless of orientation of the infuser used to deliver a controlled flow rate of a bio-compatible fluid or a controlled bolus volume of a bio-compatible fluid.

Apparatus

Figure 12:
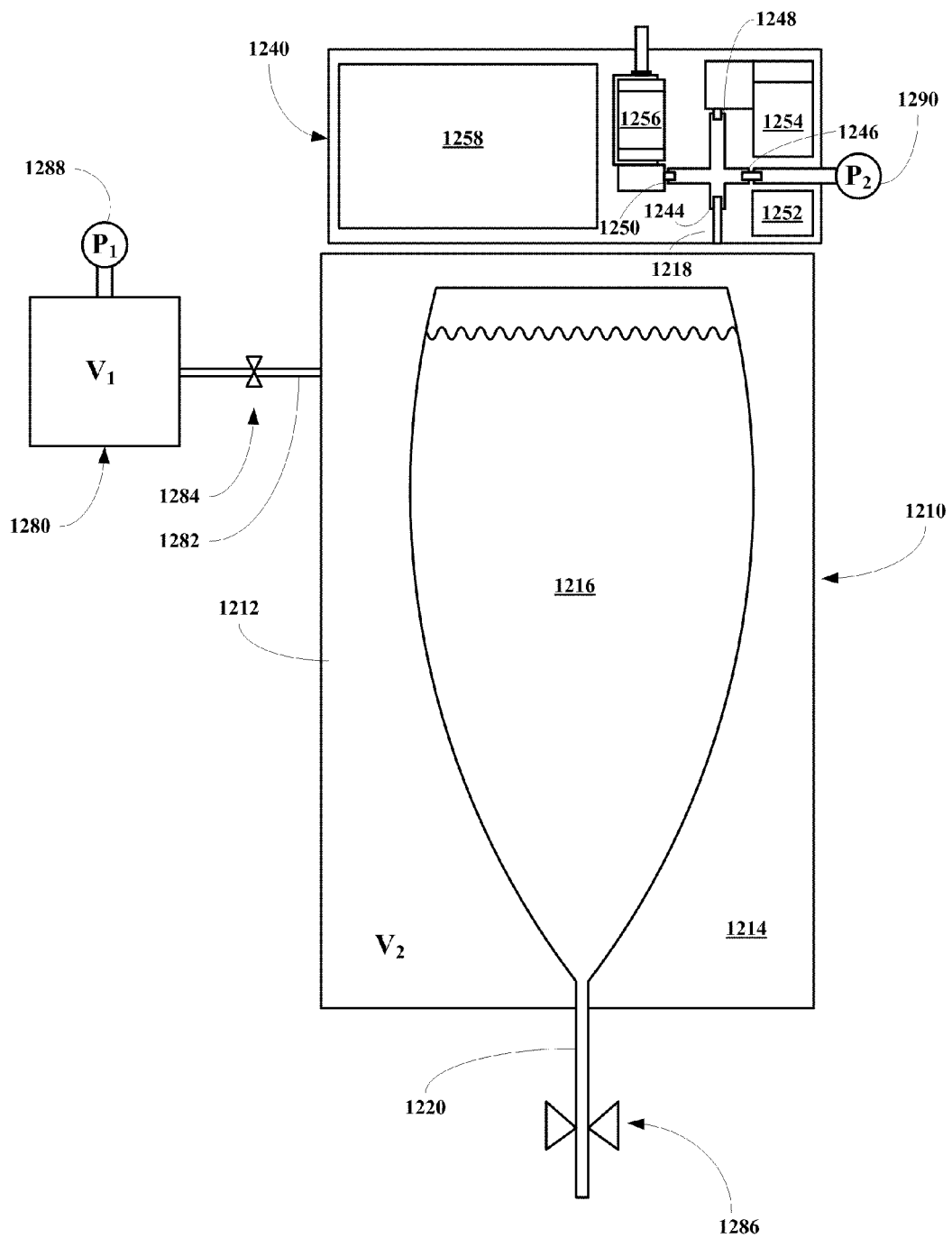
FIG. 12 depicts an embodiment of the present invention including a closed container capable of being pressurized with an IV bag disposed therein, where the apparatus is designed to accurately determine fluid flow rate and/or fluid delivery volume.

Referring now to FIG. 12, an embodiment of an apparatus of this invention, generally 1200, is shown to include an inelastic, possibly collapsible pressurization chamber 1210 and a pressurization assembly 1240 for inflating and deflating the bladder.

An interior 1214 of the inelastic, possibly collapsible pressurization chamber 1210 includes a collapsible bio-compatible fluid container 1216. The interior 1214 communicates with a pressurization/depressurization tube 1218. The bio-compatible fluid container 1216 includes an output tube 1220 adapted to supply a fluid to a patient through a pinch valve 1286. The interior 1214 contains a gas, for example air, with volume $V_2$, and bio-compatible fluid. The apparatus 1200 also includes an inelastic, possibly collapsible calibration chamber 1280 having a gas volume $V_1$ (when fully distended) in fluid communication with the interior 1214 of the container 1212 via a tube 1282 interrupted by a calibration valve 1284. The apparatus 1200 also includes a first pressure sensor 1288 for measuring the pressure $P_1$ in the calibration chamber 1280 and a second pressure sensor 1290 for measuring the pressure $P_2$ in the interior 1214.

The pressurization assembly 1240 includes a tubing network 1242 having four ends 1244, 1246, 1248 and 1250. The first end 1244 is connected to the pressurization/depressurization tube 1218. The second end 1246 is connected to a second pressure sensor 1290. The third end 1248 is connected to a pump 1254. And, the fourth end 1250 is connected to a solenoid release valve 1256. The pressurization assembly 1240 also includes control electronics 1252. The control electronics 1252 control the pump 1254 for pressurizing the interior 1214 of the chamber 1210, the solenoid release valve 1256 for depressurizing the interior 1214, a pinch valve 1286 for controlling effluent flow rate, and a calibration valve 1284, which aids in accurately estimating actual flow rate, in consideration of the pressure signals from the two pressure sensors 1288 and 1290. The pressurization assembly 1240 also includes a display 1258 for displaying data such as flow rate, bolus volume, fluid delivered over time, bladder pressure, volume remaining in the bag, and other parameters.

A calibration chamber 1280 enables measurement of volume changes or infusion rates in the incompressible bio-compatible fluid in the container 1216 as described below. By a careful control of the inflation pressure and duration via the infusion device 1254 and the release valve 1256 and a careful control of the pinch valve 1286, a controlled bolus of fluid or a precise rate of flow may be administered to the patient.

Algorithm

During pressurization of the interior 1214, the calibration valve 1284 is closed, establishing a pressure differential ($P_2 - P_1$) across the valve 1284. Both pressures $P_1$ and $P_2$ are measured at the cessation of pressurization via pressure sensors 1288 and 1290, while knowing the volume $V_1$ of the calibration chamber 1280. The calibration valve 1284 is opened, which allows the pressures across the calibration value 1284 to equalize. The pressure sensors 1288 and 1290 measure the resulting pressures $P_1$ and $P_2$. Conservation of mass is used to solve Boyle's Law for the volume $V_2$ of the compressible volume (gas) of the interior 1214.

$$V_2 = -\frac{\Delta P_1}{\Delta P_1}V_1$$

It should be noted that including temperature sensors in the calibration chambers 1280 and the interior bladder 1214 may improve the accuracy of $V_2$ slightly, using the ideal gas law as a more general form of Boyle's Law also accounting for the effects of temperature. During infusion, the mass of compressible gas within the interior 1214 is constant, hence $P_2 \cdot V_2$ is also constant according to Boyle's Law. The change in $V_2$ is then found by:

$$V_2(t) = \frac{P_2(0)}{P_2(t)}V_2(0)$$

Illustrative Use

In this illustrative example, the apparatus 1200 is used to infuse a 250 mL bolus of a bio-compatible fluid such as normal saline from a newly opened nominally 1000 mL collapsible IV bag 1216. The IV bag 1216 of our example actually contains 1035 mL of the bio-compatible fluid (normal saline) and 70 mL of gas in a plastic shell having a volume of 45 mL. The surrounding bladder assembly 1210 has a total interior volume 1214 of 1500 mL. As a composite structure, the assembly 1210 includes 1035 mL of the bio-compatible fluid (normal saline), 45 mL of the plastic bag, and 420 mL gas (70 mL from inside the IV bag and 350 mL within the bladder interior 1214). The apparatus 1200 also includes the gas calibration chamber 1280 having a volume of 200 mL. In order to achieve the requested flow rate, the driving pressure is roughly controlled between +270 mmHg and +300 mmHg.

The following preferred infusion device gas bladder inflation sequence is presented:

Step 1

Open the calibration valve 1284; close the pinch valve 1286, and use the gas pump 1254 to pressurize the calibration chamber 1280 and bladder interior 1214 to a common pressure, preferably equal to the low pressure set point for driving pressure. Continuing our example, the calibration chamber 1280 and interior bladder 1214 are pressurized to +270 mmHg=+36 kPa=137 kPa (absolute).

Step 2

Close the calibration valve 1284.

Step 3

Select a pre-inflation pressure. A preferred method that allows for the fluid bag size to be determines automatically is to measure the electric work expended by the gas pump 1254 in Step 1 and compare the amount to known values: (a) to pressurize 600 mL gas or air (typical for 1000 mL bag), the pre-inflation pressure is equal to +315 mmHg; (b) during iteration, if $V_2$<800 mL, then the pre-inflation pressure is equal to +310 mmHg; (c) to pressurize 1100 mL air (typical for 500 mL bag), the pre-inflation pressure is equal to +305 mmHg; or (d) to pressurize 1400 mL air (typical for 200 mL bag), the pre-inflation pressure is equal to +305 mmHg.

Step 4

Although the air volume cannot be determined accurately from work due to changes in room temperature, gas or air pump efficiency, etc., distinguishing these choices is possible. To illustrate the method, we select outcome a of Step 3, i.e., 600 mL air.

Step 5

Pressurize the container 1212 to the selected pre-infusion pressure (e.g., +315 mmHg), while the calibration chamber 1280 remains at the low set point pressure (e.g., +270 mmHg).

Step 6

Using the pressure sensors 1288 and 1290, precisely measure the first pressure $P_1$ and the second pressure $P_2$ to yield, for example, +269.3 mmHg and +315.8 mmHg, respectively.

Step 7

Open the calibration value 1284.

Step 8

Using the pressure sensors 1288 and 1290, precisely measure and monitor the pressures $P_1$ and $P_2$ until the difference, $\Delta P = P_2 - P_1$, is less than a threshold value of $P_2 - P_1$. In our example, the $\Delta P$ is less than 2 mmHg. The $\Delta P$ threshold value can also be less have 1 mmHg or less than 0.5 mmHg.

Step 9

Once the $\Delta P$ is less than the $\Delta P$ threshold value, $P_1$ and $P_2$ are measured precisely, yielding for example +299.2 mmHg and +301.6 mmHg, respectively.

Step 10 the volume $V_2$ is determined by simultaneous application of conservation of mass and Boyle's Law as described above, which yields a value of 421.1 mL, in our example.

Step 11

Next, the pinch valve 1284 is opened to start infusion.

Step 12

During infusion, the product of the second pressure $P_2$ and the container volume $V_2$ is assumed to be constant as described above.

Step 13

When the interior bladder pressure $P_2$ measured at the sensor 1290 decays to the low set point pressure, which in our example is +270 mmHg, repeat from Step 2 ($V_2$=470.4 mL).

Step 14

In the second iteration, $P_1$ and $P_2$ are (+270 mmHg, +310 mmHg) in Step 6 and equalize to (+298 mmHg) in Step 8. $V_2$ is estimated at 470 mL.

The volume infused is then the change in $V_2$, $\Delta V_2$. The average flow rate is the change in $V_2$, $\Delta V_2$, divided by the intervening time, $\Delta t$ or flow rate $Q = \Delta V_2/\Delta t$. The total container volume (1500 mL) less the air volume estimate (421 mL start/470 mL at the end of Step 13) and a conservative standard value for the bag plastic (70 mL) gives an estimate of a volume remaining in the IV bag (1009 mL start/960 mL at the end of Step 13) accurate enough for clinical use and generation of a IV bag change alarm.

While the above method has been derived using a closed system where the container is pressurized with the IV bag inside, the same calculation can be applied to any of the systems disclosed herein, provided the apparatus includes a calibration chamber in addition to an inelastic bladder assembly and a pressurization assembly or an inelastic bladder assembly, a pressurization assembly, and a flow control assembly. Thus, the above method can be used to accurately predict infused volume, flow rate, and fluid volume remaining.

MATERIAL IN PROVISIONAL

Displayed Information Concerning Fluid Balance

Figure 13:
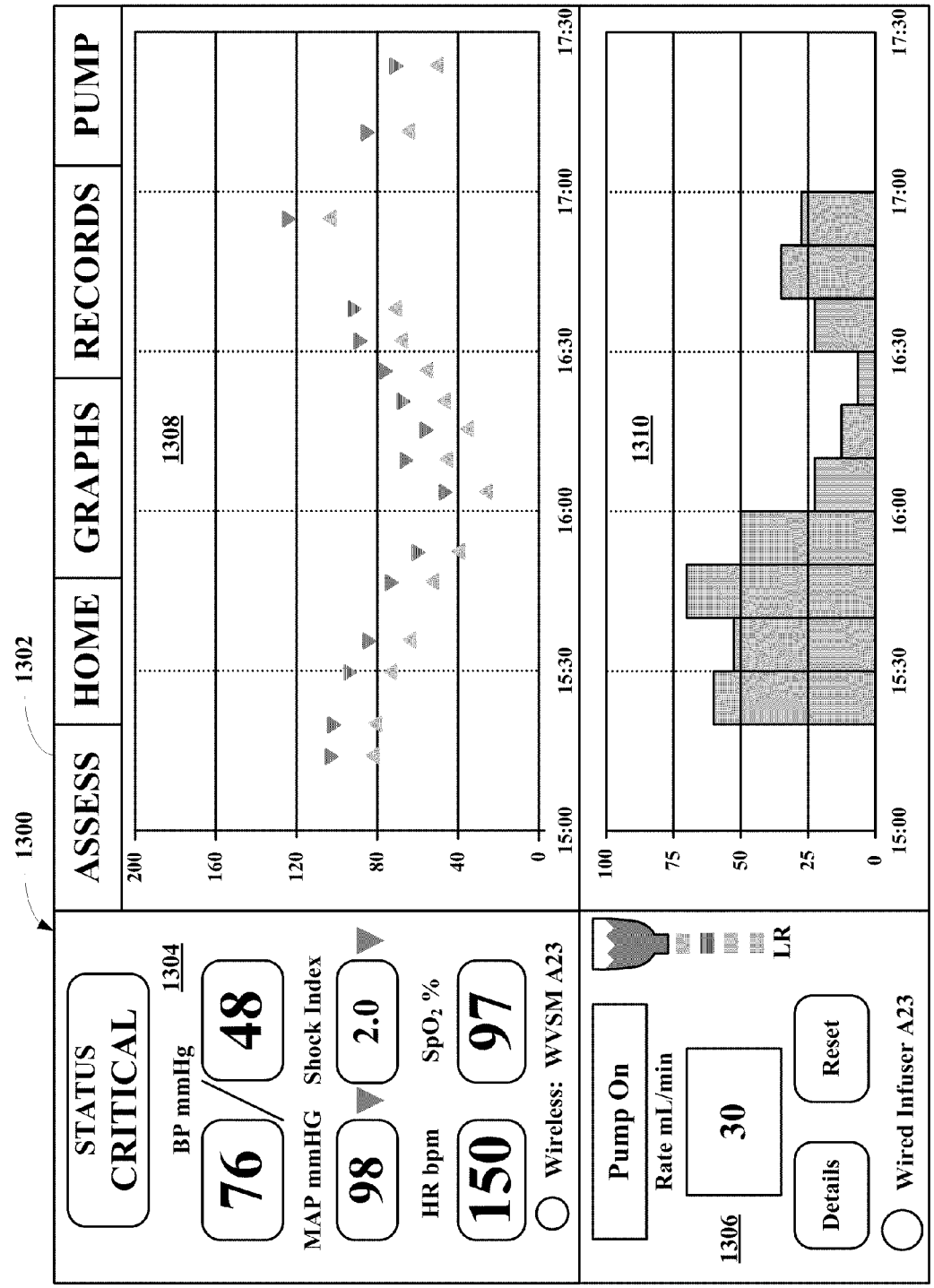
FIG. 13 depicts an embodiment of a display of the present invention, which may be associated with any of the apparatus of this invention.

Referring now to FIG. 13, an exemplary embodiment of a monitor of this invention, generally 1300 is shown. The monitor 1300 includes a display 1302, such as an LCD or other similar display. The display 1302 is divided into four information-control sections 1304, 1306, 1308, and 1310. The display 1302 may be used to output information to an operator or other medical personnel such as the current infusion rate, infused volume and the time course of the infused volume as shown in section 1310. The display 1302 may also be used to display current key vital signs as shown in section 1304 (upper left section) and the time course of one or more vital signs as shown in section 1308 (upper right section). Concurrent display of fluid therapy and the response of one or more vital signs to fluid therapy provide an aid to clinical decision making that may be used to decide on an appropriate infusion rate and volume to best restore and control the vital sign for a patient's beneficial clinical outcome. Further, the display 1302 may include a button driven menu that allows infusion rates to be adjusted up or down, allows infusion rates to be set at a precise level, or allows an infusion program to be selected that varies infusion rates per a pre-defined timed course or pre-defined protocol or allows other pump or monitoring functions to be invoked as shown in section 1306. Further, buttons or menu options may allow access to a variety of other displays such as other vital signs or fluid graphs, records, tables or advanced pump features to include decision support, semi-autonomous, and full autonomous closed loop controllers. Such screens may allow input from caregivers and administrators for a variety of functions.

Figure 14:
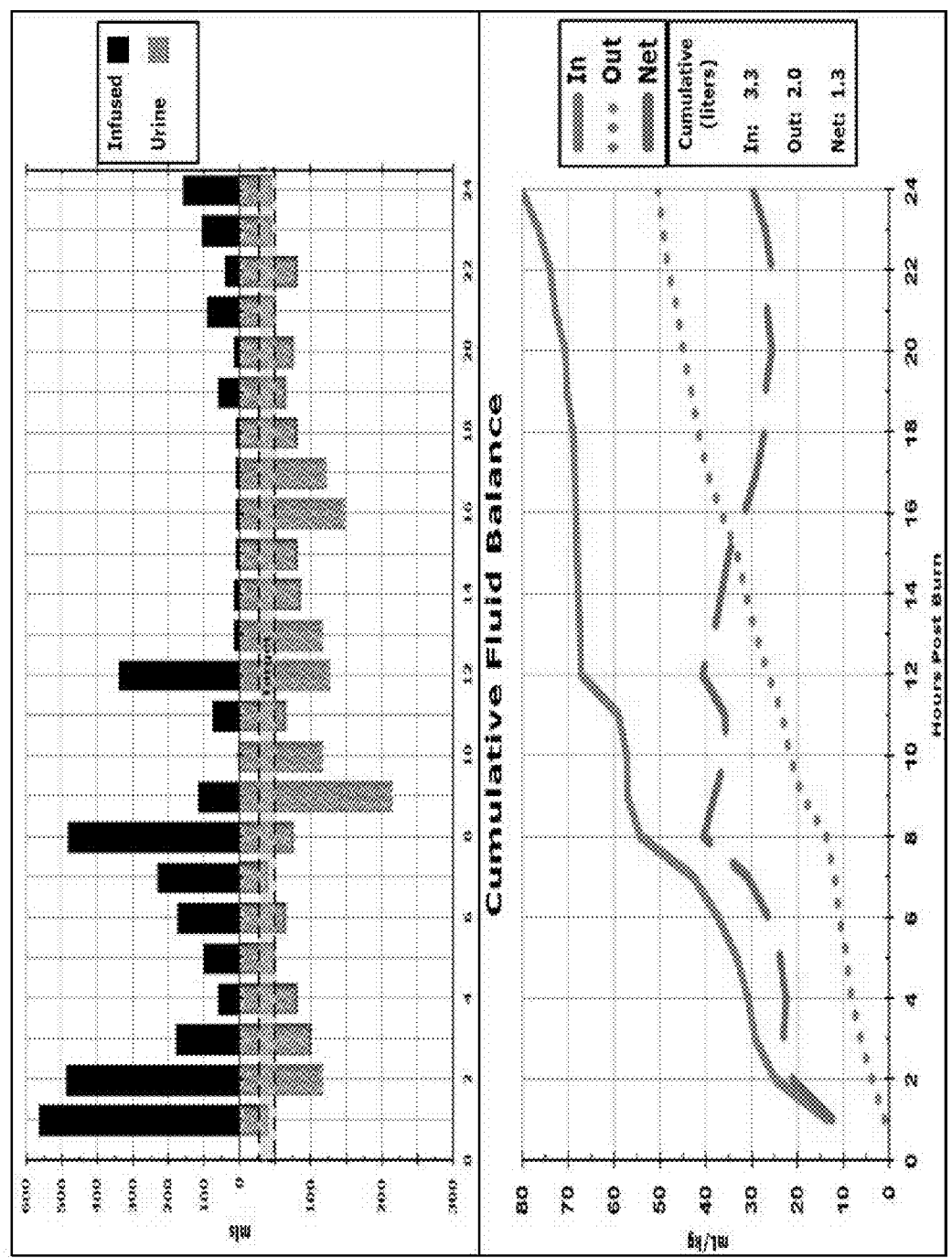
FIG. 14 depicts another embodiment of a display of the present invention, which may be associated with any of the apparatus of this invention.

Referring now to FIG. 14, a schematic diagram of a display from a fluid delivery system of this invention with a fluid infusion component and controller, and a fluid balance display. FIG. 14 is an exemplary display of output derived from a monitor for body compatible fluids and a monitor for body fluids showing an output of body fluids plotted two different ways. The graphs shown in FIG. 14 provide the time course history of hourly and cumulative infused volume and urinary outs and net fluid balance. The inputs can be used to provide comparisons of infusion therapy to physiologic responses using such as tables, graphs and charts in order for medical personnel to decide and refine the infusion rate into the patient. It is obvious to those skilled in the art that urinary output and blood pressure are only examples of physiologic or clinical variables that respond to fluid therapy. Without limitation, the embodiments shown in FIG. 13 and FIG. 14 could display real time and the time course of vital signs (central venous pressure, heart rate, pulse pressure) or derived vital signs (pulse pressure variability, shock indices, heart rate complexity metrics).

The upper and lower graphics in Display of FIG. 13 and FIG. 14 will be described in conjunction with each other. The effective result of such charts and graphs is to provide a "resuscitation display" that shows the input of the rates and volumes infused into the patient and the associated physiologic and clinical response output, such as blood pressure, FIG. 13, or urinary output, FIG. 14. Other tables, charts and/or graphs may be developed and used in conjunction with each other to provide input of fluid volume and the physiologic and clinical response such as blood pressure, other vital signs, clinical variables and physiologic variables, as would be known to those with ordinary skill in the art given the disclosure contained here. For burn patients, the urinary output is particularly important to avoid potential over-resuscitation and under-resuscitation as has been described above. The resuscitation display of FIG. 14 is a particular example, which is a "fluid balance monitor". The charts and graphs of a fluid balance monitor may include, for example, urinary output per hour post burn in comparison to upper and lower target ranges that might be predetermined as optimal for the person's particular size, age and other physiological parameters. Further, the charts may include a comparison of the infused rates with the urinary output in terms of total fluid volume with diagrams showing the overall increase or decrease of net fluid. FIG. 14 bottom chart on the display particularly can show medical personnel when the patient's cumulative infused volume and cumulative urinary output volume. In addition, the cumulative net fluid is shown and is a measure of absorbed fluid (infused minus urinary output) and is an index for the severity of the injury and is useful as an index of "over-resuscitation". When cumulative net fluid starts to decrease, it is an indicator that the resuscitation phase of burn care is ending.

CLOSING PARAGRAPH

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. A fluid delivery system comprising:
    a collapsible container including a bio-compatible fluid,
    a flow path leading from the container to a patient,
    a pressurizing assembly surrounding all or a portion of the container,
    a pressurization assembly, where the pressurization assembly pressurizes the pressurizing assembly in a controlled manner resulting in a force exerted on the container and a fluid flow rate from the container through the flow path to the patient and where the pressurization assembly depressurizes the pressurizing assembly in either a rapid manner to rapidly reduce the force on the container and the fluid flow rate from the container or to reduce the force on the container and the fluid flow rate from the container in a controlled manner, and
    a weighing assembly, where the weighing assembly weighs the container and the pressurizing assembly on an intermittent basis, periodic basis, semi-continuous basis, continuous basis or any combination of intermittent, periodic, semi-continuous, or continuous basis to measure and/or monitor a flow rate of fluid from the container and through the flow path to the patient.

2. The system of claim 1, further comprising:
    a flow control assembly, where the flow control assembly further controls the flow rate of fluid flowing from the container through the flow path to the patient.

3. The system of claim 1, wherein the pressurizing assembly comprises:
    a bladder and a sleeve,
    where the bladder and the sleeve form a pocket into which the container is placed so that the bladder and sleeve surround all or a portion of the container so that as the bladder is inflated, the bladder and the sleeve cooperate to produce the force on the container.

4. The system of claim 1, wherein the pressurizing assembly comprises:
    a housing including:
        an interior cavity for receiving the container,
        a bladder disposed on a back portion of the housing, and
        an openable door,
    where the housing surrounds all or a portion of the container so that as the bladder is inflated, the bladder and the housing cooperate to produce the force on the container.

5. The system of claim 1, wherein the pressurizing assembly comprises:
    a housing including:
        an interior cavity for receiving the container, and
        an openable door,
    where the housing surrounds the container so that as the container is pressurized, the housing produces the force on the container.

6. A fluid delivery system comprising:
    a collapsible container including a bio-compatible fluid,
    a flow path leading from the container to a patient,
    a pressurizing assembly surrounding all or a portion of the container, and
    a pressurization assembly, where the pressurization assembly pressurizes the pressurizing assembly in a controlled manner resulting in a force exerted on the container and a fluid flow rate from the container through the flow path to the patient and where the pressurization assembly depressurizes the pressurizing assembly in either a rapid manner to rapidly reduce the force on the container and the fluid flow rate from the container or to reduce the force on the container and the fluid flow rate from the container in a controlled manner,
    wherein the pressurization assembly includes an air pump, a tube connecting the pump to the pressurizing assembly, a pump control unit and a battery unit, where the pressurization assembly changes an internal pressure of the pressurizing assembly, and where the pressurization assembly sets the force exerted on the container by increasing an internal pressure of the pressurizing assembly to a set point pressure, intermittently sets the internal pressure to at least one desired pressure, periodically, semi-continuously and/or continuously varies the pressure according to a pressure change protocol and where increasing or decreasing the pressure, increases or decreases the fluid flow rate.

7. The system of claim 6, wherein the pressurization assembly further includes a pressure relief valve that when activated, will either rapidly reduce the internal pressure in the pressurizing assembly or reduce the internal pressure in the pressurizing assembly in a controlled manner.

8. The system of claim 1, wherein the weighing assembly includes a connector for detachably connecting the pressurizing assembly to the weighing assembly and a weight measuring unit for measuring the weight of the pressurizing assembly, where the weighing assembly monitors and/or measures a volume of fluid delivered from the container to the patient.

9. The system of claim 8, wherein the system is of a unitary construction.

10. The system of claim 8, wherein the system is of a modular construction.

11. A fluid delivery system comprising:
a collapsible container including a bio-compatible fluid,
a flow path leading from the container to a patient,
a pressurizing assembly surrounding all or a portion of the container,
a pressurization assembly, where the pressurization assembly pressurizes the pressurizing assembly in a controlled manner resulting in a force exerted on the container and a fluid flow rate from the container through the flow path to the patient and where the pressurization assembly depressurizes the pressurizing assembly in either a rapid manner to rapidly reduce the force on the container and the fluid flow rate from the container or to reduce the force on the container and the fluid flow rate from the container in a controlled manner, and
a flow control assembly, where the flow control assembly further controls the flow rate of fluid flowing from the container through the flow path to the patient, and wherein the flow control assembly includes a flow control valve and flow control circuitry to regulate the flow rate of fluid through the valve, permitting improved flow control of fluid being delivered to the patient.

12. The system of claim 11, wherein the system is of a unitary construction.

13. The system of claim 11, wherein the system is of a modular construction.

14. A fluid delivery system comprising:
a collapsible container including a bio-compatible fluid,
a flow path leading to a patient,
a pressurizing assembly surrounding all or a portion of the container, and
a pressurization assembly that includes an air pump, a tube connecting the pump to the pressurizing assembly, a pump control unit and a battery unit, where the pressurization assembly changes an internal pressure of the pressurizing assembly, where the pressurization assembly sets the force exerted on the container by increasing an internal pressure of the pressurizing assembly to a set point pressure, intermittently sets the internal pressure to at least one desired pressure, periodically, semi-continuously and/or continuously varies the pressure according to a pressure change protocol and where increasing or decreasing the pressure, increases or decreases the fluid flow rate, and
a weighing assembly that includes a connector for detachably connecting the pressurizing assembly to the weighing assembly and a weight measuring unit for measuring the weight of the pressurizing assembly, where the weighing assembly monitors and/or measures a volume of fluid delivered from the container to the patient and where the weighing assembly weighs the pressurizing assembly on an intermittent basis, periodic basis, semi-continuous basis, continuous basis or any combination of intermittent, periodic, semi-continuous, or continuous basis.

15. The system of claim 14, wherein the pressurizing assembly comprises:
a bladder and a sleeve,
where the bladder and the sleeve form a pocket into which the container is placed so that the bladder and sleeve surround all or a portion of the container so that as the bladder is inflated, the bladder and the sleeve cooperate to produce the force on the container.

16. The system of claim 14, wherein the pressurizing assembly comprises:
a housing including:
an interior cavity for receiving the container,
a bladder disposed on a back portion of the housing, and
an openable door,
where the housing surrounds all or a portion of the container so that as the bladder is inflated, the bladder and the housing cooperate to produce the force on the container.

17. The system of claim 14, wherein the pressurizing assembly comprises:
a housing including:
an interior cavity for receiving the container, and
an openable door,
where the housing surrounds container so that as the container is pressurized, the housing produces the force on the container.

18. The system of claim 14, wherein the system is of a unitary construction.

19. The system of claim 14, wherein the system is of a modular construction.

20. A fluid delivery system comprising:
a collapsible container including a bio-compatible fluid,
a flow path leading to a patient,
a pressurizing assembly surrounding all or a portion of the container, and
a pressurization assembly that includes an air pump, a tube connecting the pump to the pressurizing assembly, a pump control unit and a battery unit, where the pressurization assembly changes an internal pressure of the pressurizing assembly, and where the pressurization assembly sets the force exerted on the container by increasing an internal pressure of the pressurizing assembly to a set point pressure, intermittently sets the internal pressure to at least one desired pressure, periodically, semi-continuously and/or continuously varies the pressure according to a pressure change protocol and where increasing or decreasing the pressure, increases or decreases the fluid flow rate, and
a weighing assembly that includes a connector for detachably connecting the pressurizing assembly to the weighing assembly and a weight measuring unit for measuring the weight of the pressurizing assembly, where the weighing assembly monitors and/or measures a volume of fluid delivered from the container to the patient and where the weighing assembly weighs the pressurizing assembly on an intermittent basis, periodic basis, semi-continuous basis, continuous basis or any combination of intermittent, periodic, semi-continuous, or continuous basis, and a flow control assembly that includes a flow control valve and flow control circuitry to regulate the flow rate of fluid through the valve, permitting improved flow control of fluid being delivered to the patient.

21. The system of claim 20, wherein the pressurizing assembly comprises:
a bladder and a sleeve,
where the bladder and the sleeve form a pocket into which the container is placed so that the bladder and sleeve surround all or a portion of the container so that as the bladder is inflated, the bladder and the sleeve cooperate to produce the force on the container.

22. The system of claim 20, wherein the pressurizing assembly comprises:
a housing including:
an interior cavity for receiving the container,
a bladder disposed on a back portion of the housing, and
an openable door,
where the housing surrounds all or a portion of the container so that as the bladder is inflated, the bladder and the housing cooperate to produce the force on the container.

23. The system of claim 20, wherein the pressurizing assembly comprises:
a housing including:
an interior cavity for receiving the container, and
an openable door,
where the housing surrounds the container so that as the container is pressurized, the housing produces the force on the container.

24. The system of claim 20, wherein the system is of a unitary construction.

25. The system of claim 20, wherein the system is of a modular construction.

* * * * *